(12) United States Patent
MacEwan

(10) Patent No.: US 11,596,717 B2
(45) Date of Patent: *Mar. 7, 2023

(54) THREE DIMENSIONAL ELECTROSPUN BIOMEDICAL PATCH FOR FACILITATING TISSUE REPAIR

(71) Applicant: Washington University, St. Louis, MO (US)

(72) Inventor: Matthew R. MacEwan, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/576,058

(22) Filed: Jan. 14, 2022

(65) Prior Publication Data
US 2022/0249743 A1 Aug. 11, 2022

Related U.S. Application Data

(60) Continuation of application No. 17/381,792, filed on Jul. 21, 2021, now Pat. No. 11,253,635, which is a
(Continued)

(51) Int. Cl.
A61L 31/04 (2006.01)
D01D 5/00 (2006.01)
(Continued)

(52) U.S. Cl.
CPC ............... A61L 31/04 (2013.01); A61L 15/26 (2013.01); A61L 15/44 (2013.01); A61L 15/64 (2013.01);
(Continued)

(58) Field of Classification Search
USPC ......... 623/23; 424/423, 443, 618; 427/2, 31; 264/466; 602/43; 607/3, 120
See application file for complete search history.

(56) References Cited

U.S. PATENT DOCUMENTS 2,068,703 A 1/1937 Powdermaker
3,280,229 A 10/1966 Simons
(Continued)

FOREIGN PATENT DOCUMENTS

AU 2011268321 B2 10/2015
AU 2012390291 B2 9/2017
(Continued)

OTHER PUBLICATIONS

3rd International Conference on Electrospinning Conference Program dated Aug. 4-7, 2004, www.ceramics.org/electrospin2014.
(Continued)

Primary Examiner — Lynda Salvatore
(74) Attorney, Agent, or Firm — Armstrong Teasdale LLP

(57) ABSTRACT

A three-dimensional electrospun biomedical patch includes a first polymeric scaffold having a first structure of deposited electrospun fibers extending in a plurality of directions in three dimensions to facilitate cellular migration for a first period of time upon application of the biomedical patch to a tissue, wherein the first period of time is less than twelve months, and a second polymeric scaffold having a second structure of deposited electrospun fibers. The second structure of deposited electrospun fibers includes the plurality of deposited electrospun fibers configured to provide structural reinforcement for a second period of time upon application of the three-dimensional electrospun biomedical patch to the tissue wherein the second period of time is less than twelve months. The three-dimensional electrospun biomedical patch is sufficiently pliable and resistant to tearing to enable movement of the three-dimensional electrospun biomedical patch with the tissue.

31 Claims, 12 Drawing Sheets

Related U.S. Application Data continuation of application No. 17/229,226, filed on Apr. 13, 2021, now Pat. No. 11,173,234, which is a continuation of application No. 16/872,926, filed on May 12, 2020, which is a continuation of application No. 16/540,779, filed on Aug. 14, 2019, now Pat. No. 10,682,444, which is a continuation of application No. 16/131,887, filed on Sep. 14, 2018, now Pat. No. 10,441,685, which is a division of application No. 14/429,976, filed as application No. PCT/US2012/056548 on Sep. 21, 2012, now Pat. No. 10,124,089.

(51) Int. Cl.

| | | |
|---|---|---|
| *B29C 48/18* | (2019.01) | |
| *B32B 5/02* | (2006.01) | |
| *B32B 5/26* | (2006.01) | |
| *B32B 7/02* | (2019.01) | |
| *B32B 7/12* | (2006.01) | |
| *A61L 27/18* | (2006.01) | |
| *A61L 27/54* | (2006.01) | |
| *A61L 27/58* | (2006.01) | |
| *A61L 15/26* | (2006.01) | |
| *A61L 15/44* | (2006.01) | |
| *A61L 15/64* | (2006.01) | |
| *A61L 27/60* | (2006.01) | |
| *D04H 1/728* | (2012.01) | |
| *D04H 3/16* | (2006.01) | |
| *A61F 13/02* | (2006.01) | |

(52) U.S. Cl.
CPC .............. *A61L 27/18* (2013.01); *A61L 27/54* (2013.01); *A61L 27/58* (2013.01); *A61L 27/60* (2013.01); *B29C 48/18* (2019.02); *B32B 5/022* (2013.01); *B32B 5/26* (2013.01); *B32B 7/02* (2013.01); *B32B 7/12* (2013.01); *D01D 5/0007* (2013.01); *D01D 5/0038* (2013.01); *D01D 5/0061* (2013.01); *D01D 5/0076* (2013.01); *D04H 1/728* (2013.01); *D04H 3/16* (2013.01); *A61F 13/02* (2013.01); *A61L 2300/414* (2013.01); *A61L 2400/12* (2013.01); *A61L 2400/18* (2013.01); *A61L 2430/20* (2013.01); *A61L 2430/32* (2013.01); *B32B 2250/20* (2013.01); *B32B 2262/0276* (2013.01); *B32B 2307/518* (2013.01); *B32B 2307/54* (2013.01); *B32B 2307/726* (2013.01); *B32B 2307/7265* (2013.01); *B32B 2556/00* (2013.01); *D10B 2509/00* (2013.01)

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorsclmer et al. |
| 3,740,302 A | 6/1973 | Soelmgen |
| 3,802,817 A | 4/1974 | Matsuki et al. |
| 3,849,241 A | 11/1974 | Butin et al. |
| 3,909,009 A | 9/1975 | Cvetko et al. |
| 4,044,404 A | 8/1977 | Martin et al. |
| 4,340,563 A | 7/1982 | Appel et al. |
| 4,468,428 A | 8/1984 | Early et al. |
| 4,738,740 A | 4/1988 | Pinchuk et al. |
| 4,965,110 A | 10/1990 | Berry |
| 5,024,789 A | 6/1991 | Berry |
| 5,079,080 A | 1/1992 | Schwartz |
| 5,306,550 A | 4/1994 | Nishiyama et al. |
| 5,464,450 A | 11/1995 | Buscemi et al. |
| 5,591,335 A | 1/1997 | Barboza et al. |
| 5,626,611 A | 5/1997 | Liu et al. |
| 5,795,584 A | 8/1998 | Totakura et al. |
| 5,851,937 A | 12/1998 | Wu et al. |
| 5,997,568 A | 12/1999 | Liu |
| 6,147,135 A | 11/2000 | Yuan et al. |
| 6,162,535 A | 12/2000 | Turkevich et al. |
| 6,171,338 B1 | 1/2001 | Talja et al. |
| 6,180,848 B1 | 1/2001 | Flament et al. |
| 6,183,670 B1 | 2/2001 | Torobin et al. |
| 6,265,333 B1 | 7/2001 | Dzenis et al. |
| 6,306,424 B1 | 10/2001 | Vyakarnam et al. |
| 6,391,060 B1 | 5/2002 | Ory et al. |
| 6,596,296 B1 | 7/2003 | Nelson et al. |
| 6,630,231 B2 | 10/2003 | Perez et al. |
| 6,649,807 B2 | 11/2003 | Mizutani |
| 6,685,956 B2 | 2/2004 | Chu et al. |
| 6,689,374 B2 | 2/2004 | Chu et al. |
| 6,713,011 B2 | 3/2004 | Chu et al. |
| 6,753,454 B1 | 6/2004 | Smith et al. |
| 6,790,455 B2 | 9/2004 | Chu et al. |
| 6,797,655 B2 | 9/2004 | Rudisill |
| 6,946,506 B2 | 9/2005 | Bond et al. |
| 7,134,857 B2 | 11/2006 | Andrady et al. |
| 7,172,765 B2 | 2/2007 | Chu et al. |
| 7,192,604 B2 | 3/2007 | Brown et al. |
| 7,655,070 B1 | 2/2010 | Dallas et al. |
| 7,759,082 B2 | 7/2010 | Bowlin et al. |
| 7,846,466 B2 | 7/2010 | Shea et al. |
| 7,799,262 B1 | 9/2010 | Kim |
| 7,879,093 B2 | 2/2011 | Wei et al. |
| 7,981,353 B2 | 7/2011 | Mitchell et al. |
| 8,066,932 B2 | 11/2011 | Xu |
| 8,222,166 B2 | 7/2012 | Chu et al. |
| 8,273,369 B2 | 9/2012 | Moloye-Olabisi et al. |
| 8,652,215 B2 | 2/2014 | Bellamkonda et al. |
| 8,728,463 B2 | 5/2014 | Atala et al. |
| 8,728,817 B2 | 5/2014 | Ogle et al. |
| 8,809,212 B1 | 8/2014 | Dirk et al. |
| 8,852,621 B2 | 10/2014 | Patel et al. |
| 9,074,172 B2 | 7/2015 | Johnson |
| 9,085,830 B2 | 7/2015 | Mitchell et al. |
| 9,163,331 B2 | 10/2015 | Atala et al. |
| 9,168,231 B2 | 10/2015 | Patel et al. |
| 9,345,486 B2 | 5/2016 | Zhang et al. |
| 9,393,097 B2 | 7/2016 | McCullen et al. |
| 9,476,026 B2 | 10/2016 | Arinzeh et al. |
| 9,487,893 B2 | 11/2016 | Moore et al. |
| 9,539,365 B2 | 1/2017 | Kasuga et al. |
| 9,572,909 B2 | 2/2017 | Simpson et al. |
| 9,585,666 B2 | 3/2017 | Yu et al. |
| 9,737,632 B2 | 8/2017 | Johnson et al. |
| 9,884,027 B2 | 2/2018 | Johnson |
| 9,938,373 B2 | 4/2018 | Wang et al. |
| 10,016,464 B2 | 7/2018 | Murphy et al. |
| 10,080,687 B2 | 9/2018 | MacEwan |
| 10,124,089 B2 | 11/2018 | MacEwan |
| 10,149,749 B2 | 12/2018 | MacEwan et al. |
| 10,166,315 B2 | 1/2019 | Johnson et al. |
| 10,227,568 B2 | 3/2019 | Johnson |
| 10,231,821 B2 | 3/2019 | Gabriele et al. |
| 10,233,427 B2 | 3/2019 | Johnson |
| 10,239,262 B2 | 3/2019 | Johnson |
| 10,294,449 B2 | 5/2019 | Johnson |
| 10,335,154 B2 | 7/2019 | Johnson et al. |
| 10,363,041 B2 | 7/2019 | Yu et al. |
| 10,381,672 B2 | 8/2019 | Lee et al. |
| 10,405,963 B2 | 9/2019 | McAlpine et al. |
| 10,406,346 B2 | 9/2019 | Scott-Carnell et al. |
| 10,413,574 B2 | 9/2019 | Fong et al. |
| 10,420,856 B2 | 9/2019 | Arinzeh et al. |
| 10,441,403 B1 | 10/2019 | MacEwan et al. |
| 10,441,685 B2 | 10/2019 | MacEwan |
| 10,588,734 B2 | 3/2020 | MacEwan et al. |
| 10,617,512 B2 | 4/2020 | MacEwan |
| 10,632,228 B2 | 4/2020 | MacEwan |
| 10,682,444 B2 * | 6/2020 | MacEwan ............ D01D 5/0038 |
| 10,738,152 B2 | 8/2020 | Wang et al. |

(56) References Cited

U.S. PATENT DOCUMENTS

| | | |
|---|---|---|
| 10,888,409 B2 | 1/2021 | MacEwan et al. |
| 11,000,358 B2 | 5/2021 | MacEwan et al. |
| 11,096,772 B1 | 8/2021 | MacEwan et al. |
| 11,173,234 B2 * | 11/2021 | MacEwan .............. D04H 1/728 |
| 11,253,635 B2 * | 2/2022 | MacEwan ............ D01D 5/0038 |
| 11,311,366 B2 | 4/2022 | MacEwan et al. |
| 2002/0081732 A1 | 6/2002 | Bowlin et al. |
| 2002/0090725 A1 | 7/2002 | Simpson et al. |
| 2002/0173213 A1 | 11/2002 | Chu et al. |
| 2002/0192251 A1 | 12/2002 | Collin |
| 2003/0004579 A1 | 1/2003 | Rousseau et al. |
| 2003/0054035 A1 | 3/2003 | Chu et al. |
| 2004/0013819 A1 | 1/2004 | Hou et al. |
| 2004/0018226 A1 | 1/2004 | Wnek et al. |
| 2004/0037813 A1 | 2/2004 | Simpson et al. |
| 2004/0096532 A1 | 5/2004 | Dubson et al. |
| 2004/0102614 A1 | 5/2004 | Islam et al. |
| 2005/0104258 A1 | 5/2005 | Lennhoff |
| 2005/0167311 A1 | 8/2005 | Tonsfeldt et al. |
| 2005/0222591 A1 | 10/2005 | Gingras et al. |
| 2006/0085063 A1 | 4/2006 | Shastri et al. |
| 2006/0094320 A1 | 5/2006 | Chen et al. |
| 2006/0153904 A1 | 7/2006 | Smith et al. |
| 2006/0193578 A1 | 8/2006 | Ouderkirk et al. |
| 2006/0014460 A1 | 9/2006 | Isele et al. |
| 2006/0204539 A1 | 9/2006 | Atala et al. |
| 2006/0240110 A1 | 10/2006 | Kick et al. |
| 2006/0246798 A1 | 11/2006 | Reneker et al. |
| 2006/0263417 A1 | 11/2006 | Lelkes et al. |
| 2006/0264140 A1 | 11/2006 | Andrady et al. |
| 2007/0073344 A1 | 3/2007 | Jahns et al. |
| 2007/0152378 A1 | 7/2007 | Kim |
| 2007/0155273 A1 | 7/2007 | Chu et al. |
| 2007/0225631 A1 | 9/2007 | Bowlin et al. |
| 2007/0269481 A1 | 11/2007 | Li et al. |
| 2008/0065123 A1 | 3/2008 | Yli-Urpo et al. |
| 2008/0112998 A1 | 5/2008 | Wang et al. |
| 2008/0207798 A1 | 8/2008 | Hellring et al. |
| 2008/0208358 A1 | 8/2008 | Bellamkonda et al. |
| 2008/0220042 A1 | 9/2008 | Hashi et al. |
| 2008/0237934 A1 | 10/2008 | Reneker et al. |
| 2009/0028921 A1 | 1/2009 | Arinzeh |
| 2009/0074832 A1 | 3/2009 | Zussman et al. |
| 2009/0075354 A1 | 3/2009 | Reneker et al. |
| 2009/0155326 A1 | 6/2009 | Mack et al. |
| 2009/0162468 A1 | 6/2009 | Barinov et al. |
| 2009/0171467 A1 | 7/2009 | Mann et al. |
| 2009/0202616 A1 | 8/2009 | Chong et al. |
| 2009/0214614 A1 | 8/2009 | Everland et al. |
| 2009/0228021 A1 | 9/2009 | Leung |
| 2009/0317446 A1 | 12/2009 | Tan et al. |
| 2010/0003305 A1 | 1/2010 | Pattanaik |
| 2010/0047309 A1 | 2/2010 | Lu et al. |
| 2010/0061962 A1 | 3/2010 | Li |
| 2010/0076377 A1 | 3/2010 | Ehrenreich et al. |
| 2010/0092687 A1 | 4/2010 | Sumida et al. |
| 2010/0093093 A1 | 4/2010 | Leong et al. |
| 2010/0119564 A1 | 5/2010 | Kasuga et al. |
| 2010/0120115 A1 | 5/2010 | Ogle et al. |
| 2010/0166854 A1 | 7/2010 | Michniak Kohn et al. |
| 2010/0174368 A1 | 7/2010 | Lynch et al. |
| 2010/0179659 A1 | 7/2010 | Li et al. |
| 2010/0185219 A1 | 7/2010 | Gertzman et al. |
| 2010/0190254 A1 | 7/2010 | Chian et al. |
| 2010/0233115 A1 | 9/2010 | Patel et al. |
| 2010/0273258 A1 | 10/2010 | Lannutti et al. |
| 2010/0291182 A1 | 11/2010 | Palasis et al. |
| 2010/0292791 A1 | 11/2010 | Lu et al. |
| 2010/0297208 A1 | 11/2010 | Fry et al. |
| 2010/0330419 A1 | 12/2010 | Cui et al. |
| 2010/0331980 A1 | 12/2010 | Lee et al. |
| 2011/0087277 A1 | 4/2011 | Vola et al. |
| 2011/0098826 A1 | 4/2011 | Mauck et al. |
| 2011/0101571 A1 | 5/2011 | Reneker |
| 2011/0111012 A1 | 5/2011 | Pepper et al. |
| 2011/0150973 A1 | 6/2011 | Bowlin et al. |
| 2011/0152897 A1 | 6/2011 | Bates |
| 2011/0174158 A1 | 7/2011 | Walls et al. |
| 2011/0180951 A1 | 7/2011 | Teo et al. |
| 2011/0242310 A1 | 10/2011 | Beebe, Jr. et al. |
| 2011/0280919 A1 | 11/2011 | Moloye-Olabisi et al. |
| 2011/0287082 A1 | 11/2011 | Smith et al. |
| 2012/0015331 A1 | 1/2012 | Wood et al. |
| 2012/0029654 A1 | 2/2012 | Xu et al. |
| 2012/0040581 A1 | 2/2012 | Kim |
| 2012/0123342 A1 | 5/2012 | Andrews et al. |
| 2012/0165957 A1 | 6/2012 | Everland et al. |
| 2012/0225039 A1 | 9/2012 | Li et al. |
| 2012/0265300 A1 | 10/2012 | Mauck et al. |
| 2012/0310260 A1 | 12/2012 | Hamlin et al. |
| 2012/0330437 A1 | 12/2012 | El-Kurdi et al. |
| 2013/0035704 A1 | 2/2013 | Dudai |
| 2013/0110138 A1 | 5/2013 | Hurtado |
| 2013/0115457 A1 | 5/2013 | Haynie et al. |
| 2013/0197663 A1 | 8/2013 | MacEwan et al. |
| 2013/0251762 A1 | 9/2013 | Wei et al. |
| 2013/0338791 A1 | 12/2013 | McCullen et al. |
| 2014/0030315 A1 | 1/2014 | Johnson |
| 2014/0081297 A1 | 3/2014 | Hoke et al. |
| 2014/0128345 A1 | 5/2014 | Woodrow et al. |
| 2014/0272225 A1 | 9/2014 | Johnson |
| 2014/0303727 A1 | 10/2014 | Atlas et al. |
| 2014/0322512 A1 | 10/2014 | Pham et al. |
| 2015/0045818 A1 | 2/2015 | Kim et al. |
| 2015/0132423 A1 | 5/2015 | Johnson |
| 2015/0190285 A1 | 7/2015 | MacEwan |
| 2015/0250927 A1 | 9/2015 | MacEwan |
| 2015/0297791 A1 | 10/2015 | Patel et al. |
| 2015/0342719 A1 | 10/2015 | Patel et al. |
| 2016/0022873 A1 | 1/2016 | Besner et al. |
| 2016/0083692 A1 | 3/2016 | Hardy et al. |
| 2016/0083868 A1 | 3/2016 | Park |
| 2016/0136330 A1 | 5/2016 | Benkirane-Jessel et al. |
| 2016/0302869 A1 | 10/2016 | Chopra |
| 2016/0317706 A1 | 11/2016 | Johnson |
| 2017/0095591 A1 | 4/2017 | Zuhaib et al. |
| 2017/0119886 A1 | 5/2017 | Johnson et al. |
| 2017/0182206 A1 | 6/2017 | Johnson et al. |
| 2017/0182211 A1 | 6/2017 | Raxworthy et al. |
| 2017/0319323 A1 | 11/2017 | MacEwan et al. |
| 2017/0319742 A1 | 11/2017 | Johnson et al. |
| 2017/0326270 A1 | 11/2017 | MacEwan |
| 2018/0116973 A1 | 5/2018 | Jonnson |
| 2018/0161185 A1 | 6/2018 | Kresslein et al. |
| 2018/0174367 A1 | 6/2018 | Marom et al. |
| 2018/0221537 A1 | 8/2018 | Johnson et al. |
| 2018/0237952 A1 | 8/2018 | Johnson et al. |
| 2018/0245243 A1 | 8/2018 | Krieger et al. |
| 2018/0263919 A1 | 9/2018 | Hoke et al. |
| 2018/0368917 A1 | 12/2018 | Dekel et al. |
| 2019/0015563 A1 | 1/2019 | MacEwan |
| 2019/0021837 A1 | 1/2019 | MacEwan et al. |
| 2019/0054036 A1 | 2/2019 | Johnson et al. |
| 2019/0102880 A1 | 4/2019 | Parpara et al. |
| 2019/0105128 A1 | 4/2019 | Velazquez et al. |
| 2019/0134267 A1 | 5/2019 | Francis et al. |
| 2019/0134570 A1 | 5/2019 | Pintauro et al. |
| 2019/0153398 A1 | 5/2019 | Johnson |
| 2019/0175786 A1 | 6/2019 | Cohen et al. |
| 2019/0249127 A1 | 8/2019 | Johnson |
| 2019/0269829 A1 | 9/2019 | Johnson |
| 2019/0271098 A1 | 9/2019 | Johnson et al. |
| 2019/0328393 A1 | 10/2019 | Yu et al. |
| 2019/0330419 A1 | 10/2019 | Song et al. |
| 2019/0350688 A1 | 11/2019 | Hurtado et al. |
| 2019/0365520 A1 | 12/2019 | MacEwan et al. |
| 2019/0365958 A1 | 12/2019 | MacEwan |
| 2019/0374227 A1 | 12/2019 | Johnson et al. |
| 2020/0000570 A1 | 1/2020 | MacEwan et al. |
| 2020/0060800 A1 | 2/2020 | MacEwan et al. |
| 2020/0197153 A1 | 6/2020 | MacEwan et al. |
| 2020/0229679 A1 | 7/2020 | Zhao et al. |
| 2020/0242767 A1 | 7/2020 | Zhao et al. |
| 2020/0277711 A1 | 9/2020 | Xie |

(56) References Cited

U.S. PATENT DOCUMENTS

| | | |
|---|---|---|
| 2020/0390932 A1 | 12/2020 | MacEwan |
| 2021/0001014 A1* | 1/2021 | MacEwan ............ D01D 5/0061 |
| 2021/0030525 A1 | 2/2021 | MacEwan et al. |
| 2021/0052362 A1 | 2/2021 | MacEwan et al. |
| 2021/0228782 A1* | 7/2021 | MacEwan ................ B32B 7/12 |
| 2021/0236691 A1 | 8/2021 | MacEwan |
| 2021/0267746 A1 | 9/2021 | MacEwan et al. |
| 2021/0338408 A1 | 11/2021 | MacEwan et al. |
| 2022/0175510 A1 | 6/2022 | MacEwan et al. |

FOREIGN PATENT DOCUMENTS

| | | |
|---|---|---|
| CA | 2094908 C | 2/2000 |
| CA | 2802482 A1 | 12/2011 |
| CA | 2386810 C | 9/2013 |
| CN | 102260963 A | 11/2011 |
| CN | 102691176 A | 9/2012 |
| CN | 103599562 A | 2/2014 |
| CN | 104894750 A | 9/2015 |
| DE | 102014107826 A1 | 12/2014 |
| EP | 0515522 B1 | 10/1993 |
| EP | 0571415 B1 | 7/1995 |
| EP | 0757127 A1 | 2/1997 |
| EP | 2045375 B1 | 3/2011 |
| EP | 2599858 A2 | 6/2013 |
| EP | 2582868 B1 | 3/2018 |
| EP | 2358301 B1 | 7/2019 |
| EP | 3508641 B1 | 8/2020 |
| EP | 2897561 B1 | 11/2020 |
| EP | 3741896 A1 | 11/2020 |
| GB | 1286858 A | 8/1972 |
| GB | 2181207 A | 4/1987 |
| GB | 2195251 A | 4/1988 |
| JP | H03161563 A | 7/1991 |
| JP | 3487722 B2 | 1/2004 |
| JP | 2005534828 A | 11/2005 |
| JP | 2006283241 A | 10/2006 |
| JP | 2006328562 A | 12/2006 |
| JP | 2007303021 A | 11/2007 |
| JP | 2008223186 A | 9/2008 |
| JP | 2009061109 A | 3/2009 |
| JP | 2011509786 A | 3/2011 |
| JP | 4769871 B2 | 9/2011 |
| JP | 4979264 B2 | 7/2012 |
| JP | 2012528464 A | 11/2012 |
| JP | 2013518996 A | 5/2013 |
| JP | 2013534979 A | 9/2013 |
| JP | 6295258 A | 3/2018 |
| JP | 6328672 B2 | 5/2018 |
| KR | 100439871 B1 | 7/2004 |
| KR | 20060118937 A | 11/2006 |
| KR | 1020070047873 A | 5/2007 |
| KR | 101703095 A | 10/2013 |
| SG | 186379 A1 | 1/2013 |
| SG | 11201502207W A | 4/2015 |
| WO | 1991001695 A1 | 2/1991 |
| WO | 2001027365 A1 | 4/2001 |
| WO | 2002000149 A1 | 1/2002 |
| WO | 2004016839 A1 | 2/2004 |
| WO | 2006096791 A2 | 9/2006 |
| WO | 2006123858 A1 | 11/2006 |
| WO | 2007086910 A2 | 8/2007 |
| WO | 2008069760 A1 | 6/2008 |
| WO | 2009093023 A2 | 7/2009 |
| WO | 2010041944 A1 | 4/2010 |
| WO | 2010042651 A1 | 4/2010 |
| WO | 2010112564 A2 | 10/2010 |
| WO | 2010138619 A2 | 12/2010 |
| WO | 2011095141 A1 | 8/2011 |
| WO | 2011159889 A2 | 12/2011 |
| WO | 2012080706 A2 | 6/2012 |
| WO | 2013025819 A2 | 2/2013 |
| WO | 2013050428 A1 | 4/2013 |
| WO | 2013078051 A1 | 5/2013 |
| WO | 2013106822 A1 | 7/2013 |
| WO | 2014031721 A1 | 2/2014 |
| WO | 2014046669 A1 | 3/2014 |
| WO | 2014145864 A1 | 9/2014 |
| WO | 2014152906 A2 | 9/2014 |
| WO | 2015048224 A1 | 4/2015 |
| WO | 2015116917 A1 | 8/2015 |
| WO | 2015153011 A1 | 10/2015 |
| WO | 2015157485 A1 | 10/2015 |
| WO | 2016176559 A1 | 11/2016 |
| WO | 2017024263 A1 | 2/2017 |
| WO | 2017035500 A1 | 3/2017 |
| WO | 2017044982 A1 | 3/2017 |
| WO | 2017079328 A1 | 5/2017 |
| WO | 2017196325 A1 | 11/2017 |
| WO | 2018112203 A1 | 6/2018 |
| WO | 2018144858 A1 | 8/2018 |

OTHER PUBLICATIONS

ASTM Standard F2450-10, "Guide for Assessing Microstructure of Polymeric Scaffolds for Use in Tissue-Engineered Medical Products" ASTM International, West Conshohocken, PA, 10 pages (Mar. 27, 2013).

Barbol et al., "Biocompatibility evaluation of dura mater substitutes in an animal model," Neurological Research, 23(8): 813-820 (2001).

Beachley et al., "Polymer nanofibrous structures: Fabrication, biolunctionalization, and cell interactions," Progress in Polymer Science, 35(7): 868-892 (2010).

Beheshtkhoo et al., "Fabrication and Properties of Collagen and Polyurethane Polymeric Nanofibers Using Electrospinning Techniques," Journal of Environmental Treatment Techniques, 7(4): 802-807 (2019).

Bhattarai et al. "Electrospun chitosa-based nanofibers and their cellular compatibility", Biomaterials, 26(31): 6176-6184 (2005).

Bognitzki et al., "Preparation of Fibers with Nanoscaled Morphologies: Electrospinning of Polmer Blends," Polymer Engineering and Science, 41(6): 982-989 (2001).

Bognitzki et al., "Nanostructured Fibers via Electrospinning," Advanced Materials, 13(1): 70-72 (2001).

Boland et al., "Tissue Engineering Scaffolds," Encyclopedia of Biomaterials and Biomedical Engineering, 2(L-Z): 1630-1638 (2004).

Boland et al., "Tailoring Tissue Engineering Scaffolds Using Electrostatic Proceedings Techniques: A Study of Poly(Glycolic acid) Electrospinning," Journal of Macromolecular Science, 38(12): 1231-1243 (2001).

Camposeo et al., "Lobal Mechanical Properties of Electrospun Fibers Correlate to Their Internal Nanostructure," NANO Letters, 13(11): 5056-5062 (2013).

Chakrapani et al., "Electrospinning of Type I Collagen and PCL Nanofibers Using Acetic Acid," J. Applied Polymer Science, 125(4): 3221-3227 (2012); Wiley Online Library, Feb. 1, 2012.

Chen et al., "Electrospun 3D Fibrous Scaffolds for Chronic Wound Repair," Materials, 9(4): 272 (2016).

Chen et al., "Preparation and characterization of coaxial electrospun thermoplastic polyurethane/collagen compound nanofibers for tissue engineering applications," Colloids and Surfaces B: Biointerfaces, 79(2): 315-325 (2010).

Chen et al., "Preparation and Study of TPU/Collagen Complex Nanofiber via Electrospinning," AATCC Review, 10(2): 59-63 (2010).

Cheng et al., "Engineering the Microstructure of Electrospun Fibrous Scaffolds by Microtopography," Biomacromolecules 14(5): 1349-1360 (2013) doi: 10.1021/bm302000n).

Choi et al., "Formation of interfiber bonding in electrospun poly (etherimide) nanofiber web," Journal of Materials Science, 39(4): 1511-1513 (2004).

Chong, et al., "Evaluation of electrospun PCL/gelatin nanofibrous scaffold for wound healing and layered dermal reconstruction," Acta Biomaterialia, 3(3): 321-330 (2007).

Clark et al., "Investigation of the Effect of Cell Seeding on Neotissue Formation in a Tissue Engineered Trachea," J. Pediatric Surgery, 51(1): 49-55 (2016).

(56) References Cited

OTHER PUBLICATIONS

Cole et al., "A comparative long-term assessment of four soft tissue substitutes," Aesthetic Surgery Journal, 31(6): 674-681 (2011).
Cui et al., "Controlled assembly of poly(vinyl pyrrolidone) fibers through an electric-field-assisted electrospinning method," Applied Physics A, 103(1): 167-172 (2011).
Davis, et al., "A biodegradable compsite artifical tendon," Journal of Materials Science: Materials in Medicine 3: 359-364 (1992).
Deitzel et al., "The Effect of Processing Variables on the Morphology of Electrospun Nanofibers and Textiles," Polymer, 42(1): 261-272 (2001).
Dempsey et al., "Micropatterning of Electrospun Polyurethane Fibers Through Control of Surface Topography," Macromolecular Materials and Engineering, 295(11): 990-994 (2020).
Dhandayuthapani et al., "Polymeric Scaffolds in Tissue Engineering Application: A Review," International Journal of Polymer Science, vol. 2011, Article ID 290602, (19 pages).
Diaz et al., "Fabrication of structured micro and nanofibers by coaxial electrospinning," Journal of Physics, Conference Series, 127(1): 1-8 (2008) 012008.
Ding et al., "Fabrication of blend biodegradable nanofibrous nonwoven mats via multi-jet electrospinning," Polymer, 45(6): 1895-1902 (2004).
Doshi, et al., "Electrospinning Process and Applications of Electrospun Fibers," Journal of Electrostatics, 35: 151-160 (1995).
Dubsky et al., "Nanofibers Prepared by Needleless Electrospinning Technology as Scaffolds for Wound Healing," J Materials Science: Materials in Medicine, 23(4): 931-941(2012), DOI: 10.1007/s10856-012-4577-7.
Dzenis et al., "Hierarchical nano-/micromaterials based on electrospun polymer fibers: Predictive models for thermomechanical behavior" Journal of Computer-Aided Materials Design, 3: 403-408 (1996).
Dzenis et al., "Polymer Hybrid Nano/Micro Composites," Proceedings of the American Society for Composites Ninth Technical Conference, pp. 657-665, 1994.
Fang et al., "Electrospinning: An Advanced Nanofiber Production Technology." In: H. Niu, H. Zhou and H. Wang (Eds.), Energy Harvesting Properties of Electrospun Nanofibers (1st ed. [online], pp. 1-1-1-44). IOP Publishing Ltd. (2020). https://iopscience.iop.org/book/978-0-7503-2005-4/chapter/bk978-0-7503-2005-4ch1 (Accessed Apr. 6, 2021), doi 10.1088/978-0-7503-2005-4ch1.
Figallo et al., "Micropatterned biopolymer 3D scaffold for static and dynamic culture of human fibroblasts," Biotechnology Progress, 23(1): 210-216 (2007).
Foy et al., "Allergic reaction to a bovine dural substitute following spinal cord untethering," Case Report, Journal of Neurosurgery: Pediatrics, 1(2): 167-169 (2008).
Fridrikh et al., "Controlling the Fiber Diameter during Electrospinning," The American Physical Society, 90(14): 144502 (2003).
Grafe et al., "Nanofiber Webs from Electrospinning," Nonwovens in Filtration—Fifth International Conference, Stuttgart, Germany, Mar. 2003 (5 pages).
Gibson et al., "Electrospun Fiber Mats: Transport Properties," AIChE Journal, 45(1): 190-195 (1999).
Huang et al., "Generation of Synthetic Elastin-Mimetic Small Diameter Fibers and Fiber Networks," Macromolecules 33(8): 2989-2997 (2000).
Huang et al., "A review on polymer nanofibers by electrospinning and their applications in nanocomposites," Composites Science and Technology, 63(15): 2223-2253 (2003).
Jaeger et al., "Electrospinning of Ultra-Thin Polymer Fibers," Macromolecular Symposia, 127(1): 141-150 (1998).
Ju et al., "Bilayered scaffold for engineering cellularized blood vessels," Biomaterials, 31(15): 4313-4321 (2010).
Kenawy et al., "Release of tetracycline hydrochloride from electrospun poly(ethylene-co-vinylacetate), poly(lactic acid), and a blend," Journal of Controlled Release, 81(1-2): 57-64 (2002).
Khil et al., "Novel Fabricated Matrix via Electrospinning for Tissue Engineering," Journal of Biomedical Materials Research, Part B, Applied Biomaterials, 72B(1): 117-124 (2004), https://doi.org/10.1002/jbm.b.30122.
Kidoaki et al., "Mesoscopic spatial designs of nano- and microfiber meshes for tissue-engineering matrix and scaffold based on newly devised multilayering and mixing electrospinning techniques," Biomaterials, 26(1): 37-46 (2005).
Le et al., "Engineering a Biocompatible Scaffold with Either Micrometre or Nanometre Scale Surface Topography for Promoting Protein Adsorption and Cellular Response," International Journal of Biomaterials, 2013: 1-16 (2013).
Lee et al., "Development of a composite vascular scaffolding system that withstands physiological vascular conditions," Biomaterials, 29(19): 2891-2898 (2008).
Kumar et al., "Nanofibers: Effective Generation by Electrospinning and Their Applications," Journal of Nanoscience and Nanotechnology, 12(1): 1-25 (2012).
Li et al., "Direct Fabrication of Composite and Ceramic Hollow Nanofibers by Electrospinning" Nano Letters, 4(5) 933-938 (2004).
Li, et al., "Electrospinning Nanofibers as Uniaxially Aligned Arrays and Layer-by-Layer Stacked Films" Advanced Materials, 16(4): 361-366 (2004).
Li et al., "Electrospinning of Nanofibers: Reinventing the Wheel?" Advanced Materials, 16(14): 1151-1170 (2004).
Li, et al., "Electrospinning of Polymeric and Ceramic Nanofibers as Uniaxially Aligned Arrays" Nano Letters, 3(8): 1167-1171 (2003).
Liu et al., "Tensile Mechanics of Electrospun Multiwalled Nanotube/Poly(methyl methacrylate) Nanofibers," Advanced Materials, 19(9): 1228-1233 (2007).
Liu et al., "Electrospun Fibrous Mats on Lithographically Micropatterned Collectors to Control Cellular Behaviors," Langmuir 28(49): 17134-17142 (2012), doi: 10.1021/la303490x.
Madhugiri et al., "Electrospun MEH-PPV/SBA-15 Composite Nanofibers Using a Dual Syringe Method," J. American Chemical Society, 125(47): 14531-14538 (2003).
Manavitehrani et al., "Biomedical Applications of Biodegradable Polyesters," Polymers, 8(1): Article 20, 32 pages (2016).
Martinez-Lage et al. "Accidental transmission of Creutzfeldt-Jakob disease by dural cadaveric grafts" Journal of Neurology, Neurosurgery & Psychiatry, 57(9): 1091-1094 (1994).
McClure et al., "The use of air-flow impedance to control fiber deposition patterns during electrospinning," Biomaterials, 33(3): 771-779 (2012).
McMillan et al. "Small diameter poro poly (ϵ-caprolactone) films enhance adhesion and growth of human cultured epidermal keratinocyte and dermal fibroblast cells," Tissue Engineering, 13(4): 789-798 (2007).
Merriam-Webster "FIBER" Definition downloaded from https://www.merriam-webster.com/dictionary/fiber on Jul. 11, 2021.
Mi, Fwu-Log et al. "Asymmetric chitosan membranes prepared by dry/wet phase separation: a new type of wound dressing for controlled antibacterial release," Journal of Membrane Science, 212(1-2): 237-254 (2003).
Murthy et al. "Biodegradation of Polymers," Polymer Science: A Comprehensive Reference, 9: 547-560 (2012).
Norris et al., "Electrostatic Fabrication of Ultrafine Conducting Fibers: Polyaniline/Polyethylene Oxide Blends" Synthetic Metals 114(2): 109-114 (2000).
Park et al., "Apparat for Preparing Electrospun Nanofibers: Designing and Electrospinning process for Nanofiber Fabrication," Polymer International, 56(11): 1361-1366 (2007).
Pepper et al., "Factors Influencing Poor Outcomes in Synthetic Tissue-Engineered Tracheal Replacement," Otolaryngology-Head and Neck Surgery, 161(3): 458-467 (2019).
Pham et al. "Electrospun poly (ϵ-caprolactone) microfiber and multilayer nanofiber/microfiber scaffold: characterization of scaffolds and measurement of cellular infiltration," Biomacromolecules, 7(10): 2796-2805 (2006).
Pham et al., "Electrospinning of Polymeric Nanofibers for Tissue Engineering Applications: A Review," Tissue Engineering, 12(5): 1197-1211 (2006).

(56) References Cited

OTHER PUBLICATIONS

Ramakrishna et al., "Electrospun nanofibers: solving global issues," Materials Today, 9(3): 40-50 (2006).
Rieger et al., "Designing Electrospun Nanofiber Mats to Promote Wound Healing—A Review," J. Matererials Chemistiy B, 1(36): 4531-4541 (2013).
Schneider et al., "Influence of pH on Wound-healing: A New Perspective for Wound-therapy," Archives of Dermatological Research, 298(9): 413-420 (2007).
Shin et al., "Electrospun PLGA nanofiber scaffolds for articular cartilage reconstruction: mechanical stability, degradation and cellular responses under mechanical stimulation in vitro," Journal of Biomaterials Science, Polymer Edition, 17(1-2): 103-119 (2006).
Shin et al. "Experimental characterization of electrospinning: the electrically forced jet and instabilities," Polymer, 42(25): 9955-9967 (2001).
Smith et al., "Suture-reinforced electrospun polydioxanone-elastin small-diameter tubes for use in vascular tissue engineering: a feasibility study," Acta Biomaterialia 4(1): 58-66 (2008).
Stitzel, J.D. et al., "Arterial Smooth Muscle Cell Proliferation on a Novel Biomimicking, Biodegradable Vascular Graft Scaffold," Journal of Biomaterials Applications 16(1): 22-33 (2001).
Subbiah et al. "Electrospinning of Nanofibers," J. of Applied Polymer Science, 96(2): 557-569 (2005).
Tan et al., "Tensile test of a single nanofiber using an atomic force microscope tip," Applied Physics Letters, 86(7): 073115-1:3 (2004).
Teo et al., "Electrospun scaffold tailored for tissue-specific extracellular matrix," Biotechnology Journal, 1(9): 918-929 (2006).
Thomas et al. "Electrospun bioactive nanocomposite scaffolds of polycaprolactone and nanohydroxyapatite for bone tissue engineering," Journal of Nanoscience Nanotechnology, 6(2): 487-93 (2006).
Tormala, et al., "Ultra-High-Strength absorbable self-reinforced polyglycolide (SR-PGA) composite rods for internal fixation of bone fractures: In vitro and in vivo study" Journal of Biomedical Materials Research, 25(1): 1-22 (1991).
Valizadeh et al., "Electrospinning and Electrospun Nanofibres," IET Nanobiotechnology, 8(2): 83-92 (2014).
Vaz et al. "Design of scaffold for blood vessel tissue engineering using a multiple-layering electrospinning technique," Acta Biomaterialia, 1(5): 572-582 (2005).
Wikipedia, ""Polyhydroxyethylmethacrylate,"" downloaded on Dec. 18, 2019 downloaded from https://en.wikipedia.org/wiki/Polyhydroxyethylmethacrylate (3 pages).
Wikipedia, "Polyhydroxyethylmethacrylate," downloaded Sep. 9, 2020 from https://en.wikipedia.org/wiki/Polyhydroxyethylmethacrylate (2 pages).
Wise, Histologic proof that acellular dennal matrices (ADM)-Enduragen DermaMalrix and DuraMatrix—are not repopulaled or nonviable and that AlloDerm may be repopulated but degraded synchronoly, Aesthetic Surgery Journal, 32(3): 355-358 (2012).
Wulkersdorfer et al., "Bimodal Porous Scaffolds by Sequential Electrospinning of Poly (glycolic acid) with Sucrose Particles," International Journal of Polymer Science 2010: 1-9 (2010).
Xie et al. "Radially Aligned Electrospun Nanofibers as Dural Substitutes for Wound Closure and Tissue Regeneration Applicalions," ACS Nano, 4(9): 5027-5036 (2010).
Xie, et al., "Conductive core-sheath nanofibers and their potential applications in neural tissue engineering," Adv Funct Mater, 19(14): 2312-2318 (2009).
Xie et al., "Neurites outgrowth on nanofiber scaffolds with different orders, structures, and surface properties," ACS Nano, 3(5): 1151-1159 (2009).
Xie et al., "Putting electrospun nanofibers to work for biomedical research," Macromol Rapid Commun., 29(22): 1775-1792 (2008).
Yarin, et al., "Taylor Cone and Jetting from Liquid Driplets in Electrospinning of Nanofibers," Journal of Applied Physics, 90(9): 4836-4846 (2001) https://doi.org/10.1063/1.1408260; College of Polymer Science and Polymer Engineering. 85 (2001). https://ideaexchange.uakron.edu/polymer_ideas/85.
Zerris et al. "Repair of the dura mater with processed collagen devices," Journal of Biomedical Materials Research Part B: Applied Biomaterials, 83B(2): 580-588 (2007).
Zong et al., "Structure and process relationship of electrospun bioabsorbable nanofiber membranes," Polymer, 43(16): 4403-4412 (2002).
Australian Examination Report No. 1 issued for Application No. 2012390291 dated May 31, 2017 (4 pages).
Australian Examination Report issued for Application No. 2011268321, dated Apr. 17, 2015 (4 pages).
Australian Examination Report No. 1 issued for Application No. 2016406314 dated Oct. 29, 2020 (4 pages).
Australian Examination Report No. 2 issued for Application No. 2016406314 dated Mar. 12, 2021 (3 pages).
Australian Examination Report No. 3 issued for Application No. 2016406314 dated Jul. 5, 2021 (4 pages).
Australian Examination Report No. 1 issued for Application No. 2017232208 dated Jan. 8, 2018 (4 pages).
Brazilian Technical Report for related Application No. 112012032169-2, dated Feb. 20, 2019 (4 pages).
Brazilian Technical Report for related Application No. BR112015006301-2, dated Oct. 15, 2020, 5 pages.
Canadian Examiner's Report issued for Application No. 2,885,682, dated Jun. 4, 2018 (5 pages).
Chinese Examiner's Report Issued for Application No. 201680087078.9, dated Jan. 20, 2021 with translation (28 pages).
Chinese Second Office Action Issued for Application No. 201680087078.9, dated Jul. 14, 2021 with translation (23 pages).
European Extended Search Report issued for Application No. 11796426.2, dated Mar. 27, 2014 (6 pages).
European Examination Report issued for Application No. 12884789.4 dated Feb. 13, 2018 (5 pages).
European Partial Search Report issued for Application No. 12884789.4, dated Feb. 29, 2016 (8 pages).
European Extended Search Report issued for Application No. 12884789.4, dated Jun. 16, 2016 (12 pages).
European Search Report issued for Application No. 16901840.5, dated Dec. 2, 2019 (15 pages).
European Search Report and Written Opinion for Application No. 18164340, dated May 17, 2019, (5 pages).
European Search Report and Written Opinion for application No. EP20175280.5, dated Sep. 11, 2020 (8 pages).
European Office Action issued for Application No. 16901840.5, dated Sep. 10, 2021 (9 pages).
GCC Examination Report in Application No. 2017-33397, dated Apr. 15, 2019 (4 pages).
Indian Examination Report issued for Application No. 11141/DELNP/2012, dated Jun. 21, 2018 (7 pages).
Indian First Examination Report for Application No. 2299/DELNP/2015, dated Oct. 24, 2019, (6 pages) English translation.
Indian Frist Examination Report issued for Application No. 201817046790, dated Sep. 29, 2021 (6 pages).
Japanese Office action issued for Application No. 2013-515511, dated Oct. 28, 2014 (1 page).
Japanese Office translation issued for Application No. 2015-533026, dated Jun. 27, 2017 (4 pages).
Japanese Office Action Summary issued for Application No. 2015-533026, dated Oct. 18, 2016 (5 pages).
PCT International Search Report and Written Opinion issued for Application No. PCT/2012/056548, dated Apr. 26, 2013 (12 pages).
PCT International Search Report in International Application No. PCT/16/32001, dated Aug. 11, 2016 K1 page).
PCT International Search Report and Written Opinion issued for Application No. PCT/2011/040691, dated Feb. 24, 2012 (14 pages).
PCT International Preliminary Report on Patentability for PCT/2011/040691, dated Dec. 19, 2012 (9 pages).
Singapore Search Report issued for Application No. 201209288.8, dated May 15, 2014 (17 pages).
Singapore Search and Examination Report for 2012092888, dated Jan. 30, 2015 (8 pages).
Singapore Examination Report issued for Application No. 11201502207W, dated Jun. 13, 2017 (8 pages).
U.S. Appl. No. 62/154,286, filed Apr. 29, 2015, Johnson.

(56) References Cited

OTHER PUBLICATIONS

Declaration of Gary E. Wnek, Ph.D. in Support of Petition for Inter Partes Review of U.S. Pat. No. 10,632,228 dated Jan. 2021.
Defendants' Initial Invalidity Contentions in Civil Action No. 20-980-CFC-JLH dated Nov. 4, 2021 (618 pages).
Petition for Inter Partes Review of U.S. Pat. No. 10,632,228, dated May 28, 2021 (91 pages).

* cited by examiner

506

508

THREE DIMENSIONAL ELECTROSPUN BIOMEDICAL PATCH FOR FACILITATING TISSUE REPAIR

CROSS-REFERENCE TO RELATED APPLICATIONS

This application is a continuation of U.S. patent application Ser. No. 17/381,792, filed Jul. 21, 2021, which is a continuation of U.S. patent application Ser. No. 17/229,226, now U.S. Pat. No. 11,173,234, filed Apr. 13, 2021, which is a continuation of U.S. patent application Ser. No. 16/872,926, filed May 12, 2020, which is a continuation of U.S. patent application Ser. No. 16/540,779, now U.S. Pat. No. 10,682,444, filed Aug. 14, 2019, which is a continuation of U.S. patent application Ser. No. 16/131,887, now U.S. Pat. No. 10,441,685, filed Sep. 14, 2018, which is a divisional of U.S. patent application Ser. No. 14/429,976, now U.S. Pat. No. 10,124,089, filed Mar. 20, 2015, which are incorporated herein in their entirety. U.S. patent application Ser. No. 14/429,976 is a U.S. National Phase Patent Application of International Application Serial Number PCT/US2012/056548, filed Sep. 21, 2012, which is incorporated herein in its entirety.

BACKGROUND

Numerous pathological conditions and surgical procedures result in substantial defects in a variety of organs, tissues, and anatomical structures. In the majority of such cases, surgeons and physicians are required to repair such defects utilizing specialized types of surgical meshes, materials, and/or scaffolds. Unfortunately, the in vivo performance of known surgical materials is negatively impacted by a number of limiting factors. For instance, existing synthetic surgical meshes typically result in excessive fibrosis or scarification leading to poor tissue integration and increased risk of post-operative pain. Simultaneously, known biologic materials may induce strong immune reactions and aberrant tissue ingrowth which negatively impact patient outcomes. Additionally, existing synthetic surgical meshes can create scarification, post-operative pain, limited mobility, limited range of motion, adhesions, infections, erosion, poor biomechanical properties, and/or poor intra-operative handling.

Nanofabricated or nanofiber meshes or materials composed of reabsorbable polymer fibers tens to thousands of times smaller than individual human cells have recently been proposed as a unique substrate for implantable surgical meshes and materials. Generally, existing nanofiber materials tend to possess suboptimal mechanical performance compared to known surgical meshes. Existing nanofiber materials do not possess the tensile strength, tear resistance, and burst strength needed for numerous surgical applications or for basic intraoperative handling prior to in vivo placement. To combat this deficiency, known meshes are formed using higher fiber densities as a means of improving mechanical strength. Yet, utilization of such high-density meshes can decrease effective cellular ingrowth into the mesh, decrease mesh integration with native tissue, and reduce the biocompatibility of the polymeric implant. As a result, nanofiber materials with increased thickness and/or strength and favorable cellular and/or tissue integration and biocompatibility is needed as well as a method for producing nanofiber materials.

SUMMARY

A three-dimensional electrospun nanofiber scaffold for use in repairing a defect in a tissue substrate is provided. The three-dimensional electrospun nanofiber scaffold includes a first layer formed by a first plurality of electrospun polymeric fibers and a second layer formed by a second plurality of electrospun polymeric fibers. The second layer is coupled to the first layer using a coupling process and includes a plurality of varying densities formed by the second plurality of electrospun polymeric fibers. The first and second layers are configured to degrade via hydrolysis after at least one of a predetermined time or an environmental condition. The three-dimensional electrospun nanofiber scaffold is configured to be applied to the tissue substrate containing the defect.

A three-dimensional electrospun nanofiber scaffold for use in repairing a defect in a tissue substrate is provided. The three-dimensional electrospun nanofiber scaffold includes a first plurality of electrospun polymeric fibers and a second plurality of electrospun polymeric fibers. The second plurality of electrospun polymeric fibers are coupled to the first plurality of electrospun polymeric fibers using a coupling process and form a plurality of varying densities within the three-dimensional electrospun nanofiber scaffold. The first plurality of electrospun polymeric fibers and the second plurality of electrospun polymeric fibers are configured to separate after at least one of a predetermined time or an environmental condition. The three-dimensional electrospun nanofiber scaffold is configured to be applied to the tissue substrate containing the defect.

A biomedical patch for use in repairing a defect in a tissue substrate is provided. The biomedical patch includes a first plurality of electrospun polymeric fibers and a second plurality of electrospun polymeric fibers. The second plurality of electrospun polymeric fibers are coupled to the first plurality of electrospun polymeric fibers using a coupling process and form a plurality of varying densities within the biomedical patch. The first plurality of electrospun polymeric fibers and the second plurality of electrospun polymeric fibers are configured to separate after at least one of a predetermined time or an environmental condition. The biomedical patch is configured to be applied to the tissue substrate containing the detect.

BRIEF DESCRIPTION OF THE DRAWINGS

The embodiments described herein may be better understood by referring to the following description in conjunction with the accompanying drawings.

DETAILED DESCRIPTION

Figure 1:
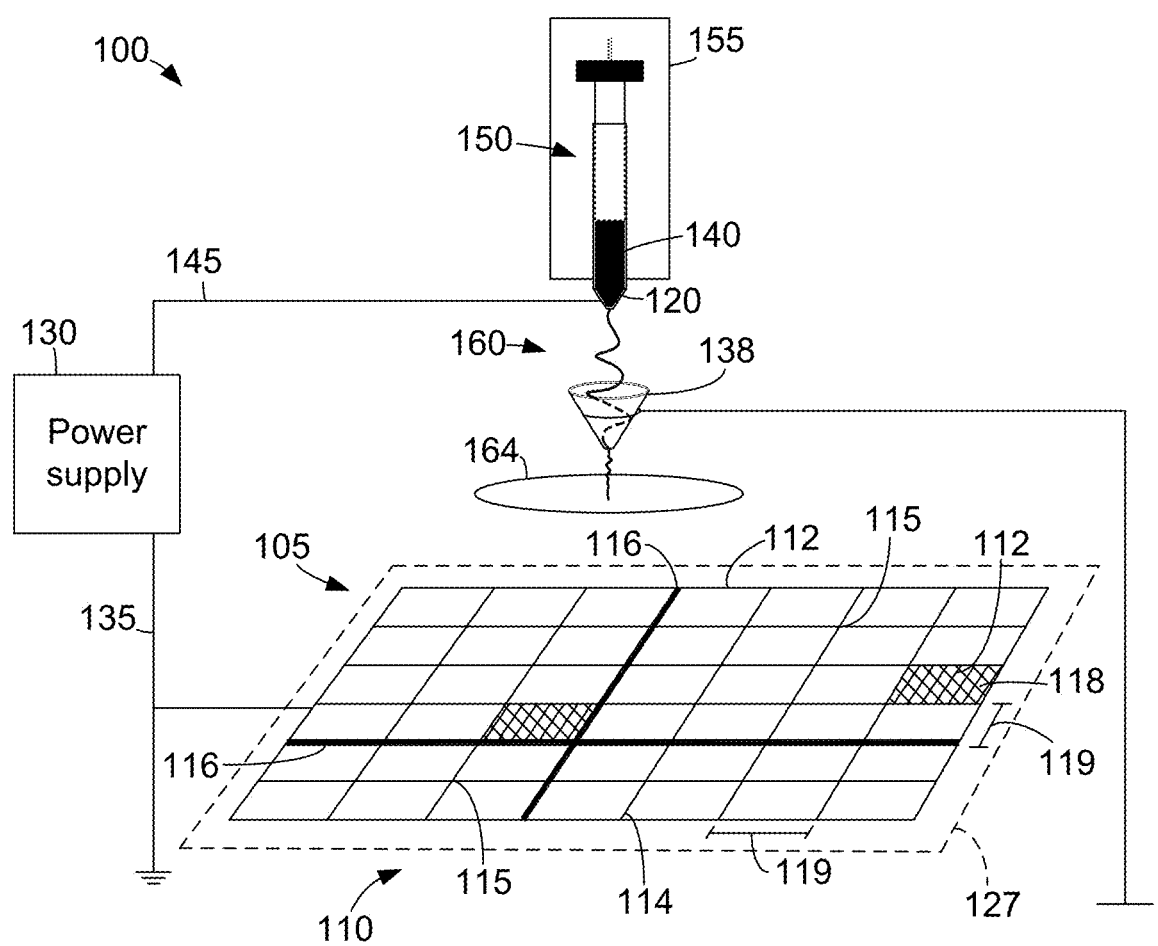
FIG. 1 is a diagram illustrating an electrospinning system for producing a structure of spatially arranged fibers.

Embodiments provided herein facilitate repairing biological tissue or reinforcing biomedical material with the use of a biomedical patch including a plurality of fibers. Such fibers may have a very small cross-sectional diameter (e.g., from 1-3000 nanometers) and, accordingly, may be referred to as nanofibers and/or microfibers. While biomedical patches are described herein with reference to dura mater and use as a surgical mesh, embodiments described may be applied to any biological tissue. Moreover, although described as biomedical patches, structures with aligned fibers may be used for other purposes. Accordingly, embodiments described are not limited to biomedical patches.

In operation, biomedical patches provided herein facilitate cell growth, provide reinforcement, and may be referred to as "membranes," "scaffolds," "matrices," "meshes", "implants", or "substrates." Biomedical patches with varying densities, as described herein, may promote significantly faster healing and/or regeneration of tissue such as the dura mater than existing patches constructed using conventional designs.

Dura mater is a membranous connective tissue comprising the outermost layer of the meninges surrounding the brain and spinal cord, which covers and supports the dural sinuses. Surgical meshes are often needed during neurosurgical, orthopedic, or reconstructive surgical procedures to repair, expand, reinforce, or replace the incised, damaged, or resected dura mater.

Although many efforts have been made, the challenge to develop a suitable surgical mesh for dural repair has been met with limited success. Autografts (e.g., fascia lata, temporalis fascia, and pericranium) are preferable because they do not provoke severe inflammatory or immunologic reactions. Potential drawbacks of autografts include the difficulty in achieving a watertight closure, formation of scar tissue, insufficient availability of graft materials to close large dural defects, increased risk of infection, donor site morbidity, and the need for an additional operative site. Allografts and xenograft materials are often associated with adverse effects such as graft dissolution, encapsulation, foreign body reaction, immunological reaction, contracture, scarring, adhesion formation, and toxicity-induced side effects from immunosuppressive regimens. Lyophilized human dura mater as a dural substitute has also been reported as a source of transmittable diseases, specifically involving prions, such as Creutzfeldt-Jakob disease.

In terms of synthetic surgical mesh materials, non-absorbable synthetic polymers, such as silicone and expanded polytetrafluoroethylene (ePTFE), often cause serious complications that may include induction of granulation tissue formation due to their chronic stimulation of the foreign body response. Natural absorbable polymers, including collagen, fibrin, and cellulose, may present a risk of infection and disease transmission. As a result, synthetic absorbable polymers such as poly (3-hydroxybutyrate-co-3-hydroxyvalerate) (PHBV), poly (lactic acid) (PLA), polyglycolic acid (PGA), poly (lactic-co-glycolic acid) (PLGA), PLA-PCL-PGA ternary copolymers, and hydroxyethylmethacrylate hydrogels have recently attracted attention as biodegradable implant materials for dural repair. Methods and systems described herein may be practiced with these materials and/or any biomedical polymer whether the polymer is non-absorbable or absorbable, or synthetic in origin.

In order to facilitate successful regeneration and/or repair of the dura mater following surgery, a synthetic surgical mesh or biomedical patch should promote: i) adhesion of dural fibroblasts (the primary cell type present in the dura) to the surface of the biomedical patch; ii) migration of dural fibroblasts from the periphery of the biomedical patch into the center of the patch; iii) reinforcement or replacement of existing tissues; iv) minimal immune response; v) water tight closure of the dural membrane/dura mater; vi) mechanical support of the native dural post-operatively and during tissue regeneration/neoduralization; vii) rapid closure of the dural defect; and viii) increased ease of use.

Electrospinning is an enabling technique which can produce nanoscale fibers from a large number of polymers. The electrospun nanofibers are typically collected as a randomly-oriented, nonwoven mat. Uniaxially or radially aligned arrays of nanofibers can also be obtained under certain conditions. However, traditional nanofiber scaffolds may lack the optimal mechanical and biological properties necessary for some biomedical or surgical applications post-operatively.

In order to increase the strength of nanofiber scaffolds, custom fabrication of scaffolds into particular patterns would be highly advantageous. Additionally, multiple layers of nanofiber materials fused/coupled together in a manner that allows for a purposeful degradation of the layers can also provide strength while allowing for cellular penetration and/or tissue integration.

Many polymers are available for use in electrospinning. In some embodiments described herein, nanofibers for dura substitutes are produced as the electrospun polymer from poly (ε-caprolactone) (PCL), an FDA approved, semicrystalline polyester that can degrade via hydrolysis of its ester linkages under physiological conditions with nontoxic degradation products. This polymer has been extensively utilized and studied in the human body as a material for fabrication of drug delivery carriers, sutures, or adhesion barriers. As described herein, electrospun PCL nanofibers may be used to generate scaffolds that are useful as surgical meshes.

Embodiments provided herein facilitate producing a novel type of artificial tissue substitute including a polymeric nanofiber material, which is formed through a novel method of electrospinning. This polymeric material includes non-woven nanofibers (e.g., fibers having a diameter of 1-3000 nanometers) which are arranged or organized and aligned into patterns both within and across a material sheet.

FIG. 1 is a diagram illustrating a perspective view of an exemplary electrospinning system 100 for producing a structure of spatially arranged or organized fibers. System 100 includes a collector 105 with a predetermined pattern 110 including a plurality of reinforcement features 112. System 100 also includes a spinneret 120.

System 100 is configured to create an electric potential between one or more collectors 105 and one or more spinnerets 120. In one embodiment, collector 105 and features 112 are configured to be electrically charged at a first amplitude and/or polarity. For example, collector 105 and features 112 may be electrically coupled to one or more power supplies 130 via one or more conductors 135. Power supply 130 is configured to charge collector 105 and features 112 at the first amplitude and/or polarity via conductor 135.

In the embodiment illustrated in FIG. 1, collector 105 includes pattern 110 that is a grid pattern formed by features 112 such that collector 105 is substantially rectangular. In other embodiments, collector 105 may have any shape including, but not limited to, circular, elliptical, ovular, square, and/or triangular. In one embodiment, features 112 include ribs 114, seams 116, and surfaces 118 configured to receive and/or collect polymer fibers. In one embodiment, rib 114 is substantially cylindrical and has a circumference between 5 um-100 cm, seam 116 is substantially rectangular having a thickness between 5 um-100 cm, and surface 118 is a filling of a void or feature space 119 formed between ribs 114 and/or seams 116. In one embodiment, surface has a thickness between 5 um-10 cm. In the exemplary embodiment, features 112 are made fabricated from at least a portion of metallic substance, including, but not limited to steel, aluminum, tin, copper, silver, gold, platinum, and any alloy or mixture thereof. In one embodiment, features 112 include a coating applied to collector 105. Coatings can include, but are not limited to anodization, chemical coatings, material coatings (conductive or non-conductive), and gradient coatings that facilitate the creation of continuous gradients of fibers. However, it should be noted that features 112 (e.g., ribs 114, seams 116, and surface 118) can have any shape and be fabricated from any material that facilitates producing patches as disclosed herein.

In the exemplary embodiment, pattern 110 is formed by spatially organizing features 112. In one embodiment, features 112 (e.g., ribs 114 and seams 116) are interconnected at nodes 115 such that a feature space 119 is formed between features 112 in the range of 10 um and 10 cm. In one embodiment, pattern 110 includes a plurality of spaces 119 such that multiple varying distances are formed between features 112. It should be noted that pattern can be formed to be symmetrical, repeating, and asymmetrical. In the exemplary embodiment, the shape of collector 105 enables the biomedical patch formed on collector to include additional support and/or reinforcement properties. Such additional support and/or reinforcement properties are achieved by creating high density fiber deposition areas on charged features 112 and having low density fiber deposition areas over feature spaces 119.

For example, a diamond shaped collector 105 including a diamond shaped array pattern 110 enables a diamond-shaped patch to be produced on the diamond shaped collector 105 to have different mechanical properties from a rectangular-shaped or a circular-shaped patch such as, but not limited to, tensile strength, tear resistance, terminal strain, failure mechanisms or rates, and/or controlled anisotropic properties, such as greater strength in one axis relative to another.

In one embodiment, pattern 110 defines a collector plane 127 and spinneret 120 is orthogonally offset from the collector plane 127 at a variable distance. For example, spinneret 120 may be orthogonally offset from the collector plane 127 at a distance of 50 micrometers to 100 centimeters. Alternatively, spinneret 120 can be offset from collector 105 in any manner that facilitates creating patches as described herein, including but not limited to, horizontal and diagonal or skew.

Spinneret 120 is configured to dispense a polymer 140 while electrically charged at a second amplitude and/or polarity opposite the first amplitude and/or polarity. As shown in FIG. 1, spinneret 120 is electrically coupled to one or more power supplies 130 by one or more conductors 145. Power supply 130 is configured to charge one or more spinnerets 120 at the second amplitude and/or polarity via conductor 145. In some embodiments, power supplies 130 provides a direct current and/or static or time variant voltage (e.g., between 1-50 kilovolts). In one embodiment, conductor 145 is charged positively, and collector 105 is also charged positively. In all embodiments, power supply 130 is configured to allow adjustment of a current, a voltage, and/or a power.

In one embodiment, spinneret 120 is coupled to a dispensing mechanism 150 containing polymer 140 in a liquid solution form. In such an embodiment, dispensing mechanism 150 is operated manually by a dispensing pump 155. Alternatively, dispensing mechanism 150 can be operated automatically with any mechanism configured to dispense nanofibers as described herein. In the exemplary embodiment, spinneret 120 includes a metallic needle having an aperture between 10 micrometers and 3 millimeters in diameter for dispensing nanofibers.

As dispensing mechanism 150 pressurizes polymer 140, spinneret 120 dispenses polymer 140 as a jet or stream 160. In one embodiment, stream 160 is dispensed in a horizontal or sideways stream from spinneret 120. Stream 160 has a diameter approximately equal to the aperture diameter of spinneret 120. Stream 160 descends toward collector 105 forming a Taylor cone. For example, stream 160 may fall downward under the influence of gravity and/or may be attracted downward by charge distributed on the fibers and on features 112. As stream 160 descends, polymer 140 forms one or more solid polymeric fibers 165. In the exemplary embodiment, fibers 165 are solid, however it should be noted that fibers 165 can have any structure including by not limited to, core or shell, porous, co-axial, and co-axial. Alternatively, polymer 140 deposition can be accomplished by any other fiber deposition method including but not limited to, solvent electrospinning, force electrospinning, melt electrospinning, extrusion, and melt blowing.

In some embodiments, a mask 164 composed of a conducting or non-conducting material is applied to collector 105 to manipulate deposition of fibers 165. For example, mask 164 may be positioned between spinneret 120 and collector 105 such that no fibers 165 are deposited on collector 105 beneath mask 164. Moreover, mask 164 may be used as a time-variant mask by adjusting its position between the spinneret and the collector while spinneret 120 dispenses polymer 140, facilitating spatial variation of fiber density on collector 105. While mask 164 is shown as circular, mask 164 may have any shape (e.g., rectangular or semi-circular) and size suitable for use with system 100. Alternatively, or in addition, deposition of fibers 165 on collector 105 may be manipulated by adjusting the position of collector 105 with respect to spinneret 120 or by spatially varying the electrical potential applied between the spinneret 120 and/or the electrodes making up the collector 105. For example, positioning one side of collector 105 directly beneath spinneret 120 may cause more fibers 165 to be deposited on that side than are deposited on the opposite side of collector 105 in a Gaussian distribution. To modulate the spatial distribution of fibers forming on collector 105, in some embodiments, a focusing device 138 is utilized to focus fiber deposition in a particular special region. In such an embodiment, focusing device 138 is charged with a polarity similar to spinneret 120 and includes an aperture allowing fiber deposition to occur substantially in the space under the aperture. Focusing device 138 may have any geometry that allows for receipt of nanofibers from spinneret 120 and deposition of the received nanofibers onto collector 105 as described herein.

Figure 2:
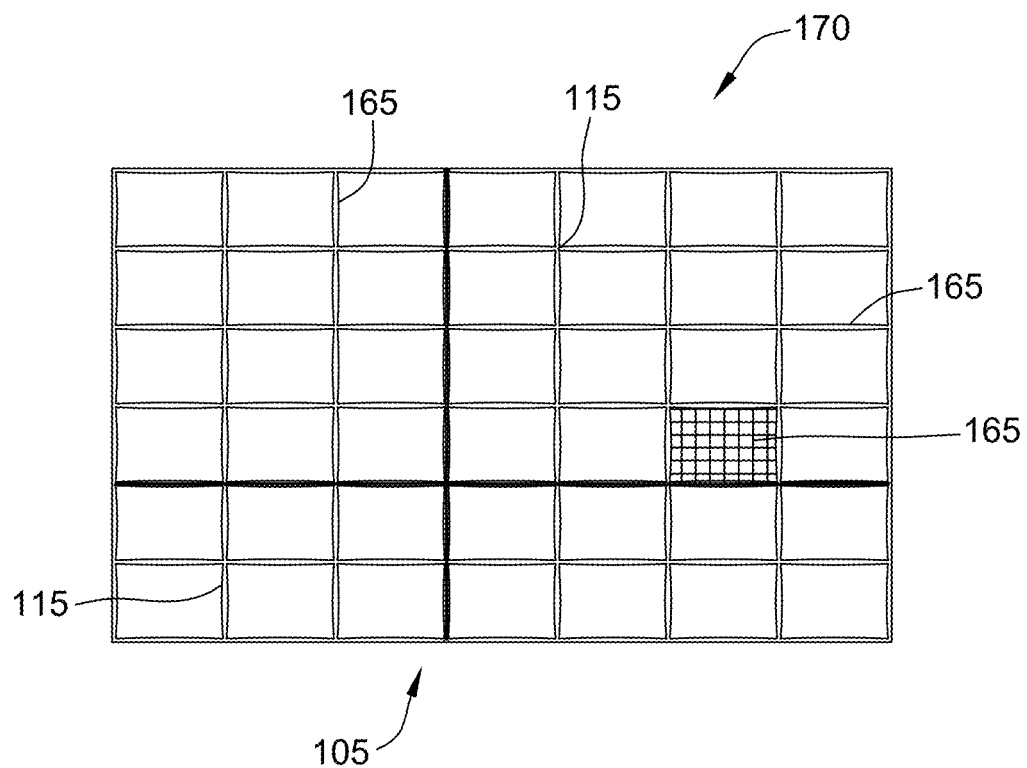
FIG. 2 is a diagram of a collector removed from the electrospinning system of FIG. 1 and having a plurality of fibers deposited thereon forming a patch.

FIG. 2 is a diagram of collector 105 removed from electrospinning system 100 (shown in FIG. 1) and having a plurality of fibers 165 deposited thereon forming a patch 170. Fibers 165 are oriented such that they correspond to the position of features 112 (shown in FIG. 1).

Patch 170 is illustrated with a small quantity of fibers 165 in FIG. 2 for clarity. In some embodiments, patch 170 includes thousands, tens of thousands, hundreds of thousands, or more fibers 165, distributed on collector 105. Even with millions of fibers 165, patch 170 retains predictable properties such as being flexible and/or pliable. As such, the predictable properties facilitate the application of patch 170 to uneven biological tissue surfaces, such as the surface of the dura mater.

The alignment of fibers 165 illustrates a patch 170 with varying densities. Patch 170 enables reinforcement or structural integrity to be provided in predetermined locations. For example, a larger deposition of fibers occurs in various locations, such as portion 167, which provide structural reinforcement. Accordingly, system 100 enables the creation of customized materials 170 for individual biomedical or clinical and non-clinical applications.

In the exemplary embodiment, fibers 165 have a diameter of 1-3000 nanometers. In one embodiment, fibers have a diameter of approximately 220 nanometers (e.g., 215 nm to 225 nm). It should be noted that the diameter of the fibers 165, thickness of the patch 170, and/or fiber density within the patch 170 may affect the durability (e.g., tensile strength, suture pullout strength, conformability, etc.) of patch 170. As such, the diameter of the fibers 165, thickness of the patch 170, and/or fiber density within the patch 170 can be selected according to the requirements of the end application of the material. Patch 170 may be produced with various mechanical properties by varying the thickness and/or the fiber density, spatial patterning, polymer composition, and/or number of layers of the patch 170 by operating electrospinning system 100 for relatively longer or shorter durations, changing the polymeric solution, changing the chemical composition, changing collector 105, changing collector design, and/or changing the manner of fiber deposition.

Figure 3:
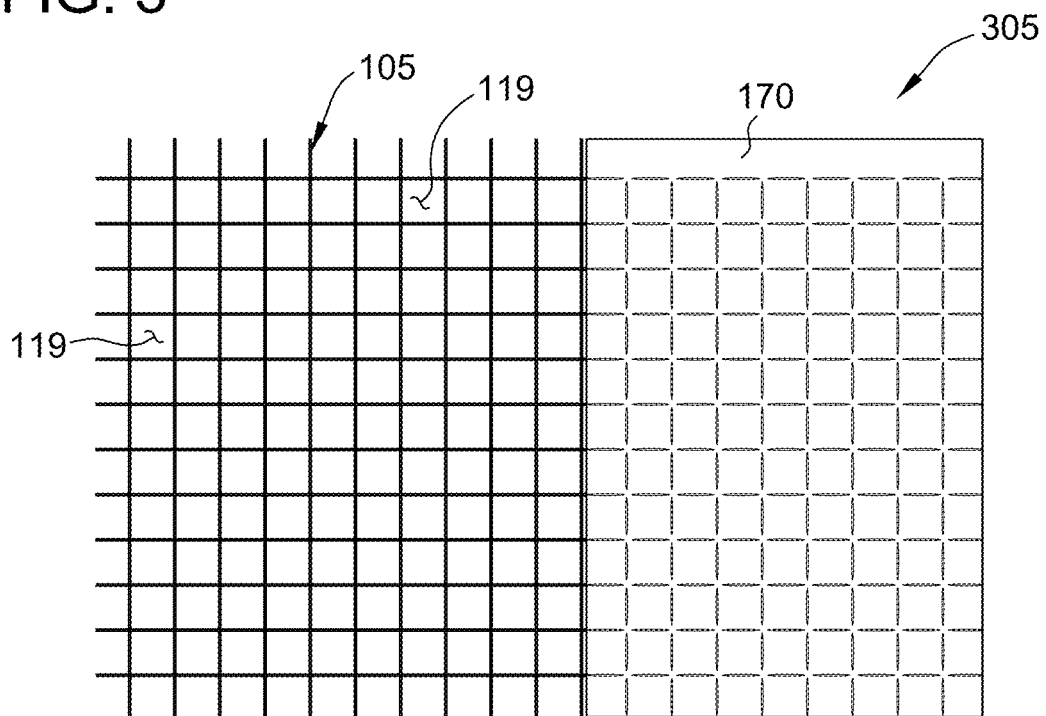
FIG. 3 is an illustration of a biomedical patch including a plurality of spatially arranged electrospun fibers deposited on a collector shown in FIG. 1.
Figure 4:
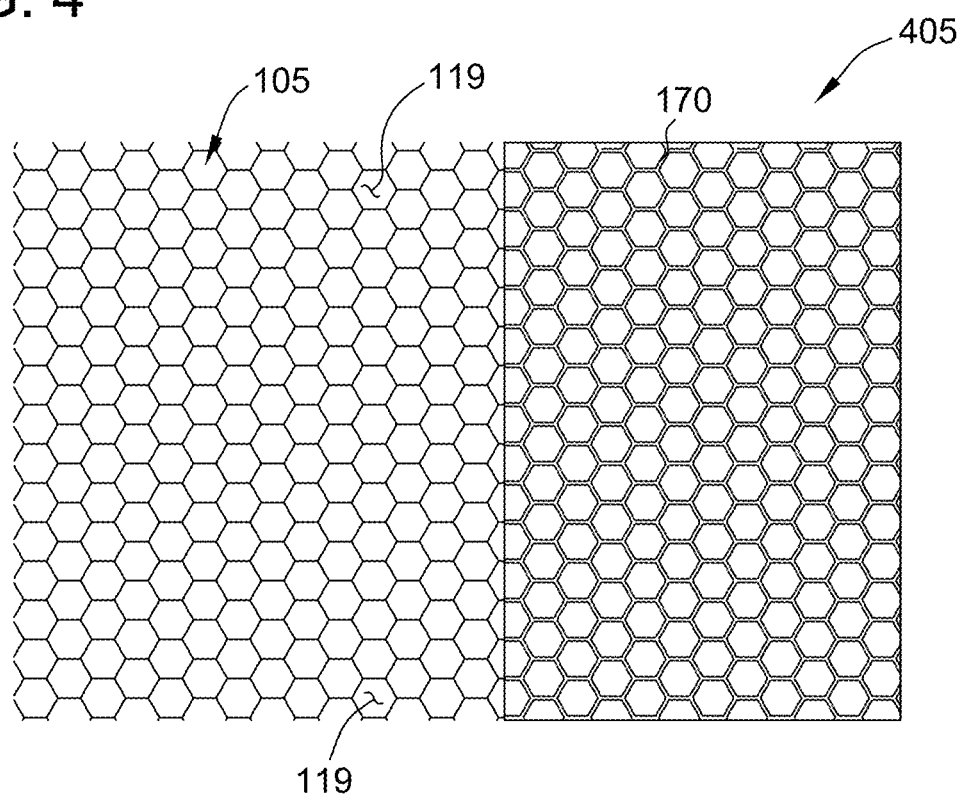
FIG. 4 is another illustration of a biomedical patch including a plurality of spatially arranged electrospun fibers deposited on a collector shown in FIG. 1.

FIG. 3 is an illustration 305 of a patch 170 including a plurality of electrospun fibers deposited on collector 105 and FIG. 4 is an illustration 405 of a patch 170 including a plurality of electrospun fibers deposited on collector 105. In the exemplary embodiment, collectors 105 respectively provide an increased deposition of fibers on and substantial near features 112. Such additional support and/or reinforcement properties are achieved by creating high density fiber deposition areas on charged features 112 and having low density fiber deposition areas over feature spaces 119. It should be noted that collector 105 can include any pattern or combination of patterns such as the grid pattern shown in FIG. 3 and the hexagonal or honeycomb pattern shown in FIG. 4.

Figure 5:
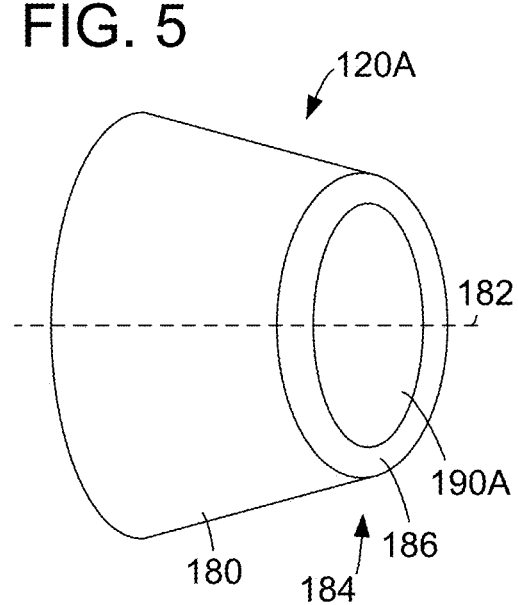
FIG. 5 is an illustration of a solid fiber spinneret shown in FIG. 1.

Referring to FIGS. 1-4, fibers 165 may be solid, core/shell, co-axial, or porous. In some embodiments, the size and/or structure of fibers 165 is determined by the design and/or size of spinneret 120, and/or polymer solution which includes viscosity, solvent or method of preparation of the solution, voltage or electric charge, distance between spinneret 120 and collector 105, and rate of deposition. FIG. 5 is an illustration of a solid fiber spinneret 120A. Solid fiber spinneret 120A includes a truncated conical body 180 defining a center line 182. At a dispensing end 184, body 180 includes an annulus 186. Annulus 186 defines a circular aperture 190A, through which polymer 140 may be dispensed. Fibers 165 produced with solid fiber spinneret 120A have a solid composition.

Figure 6:
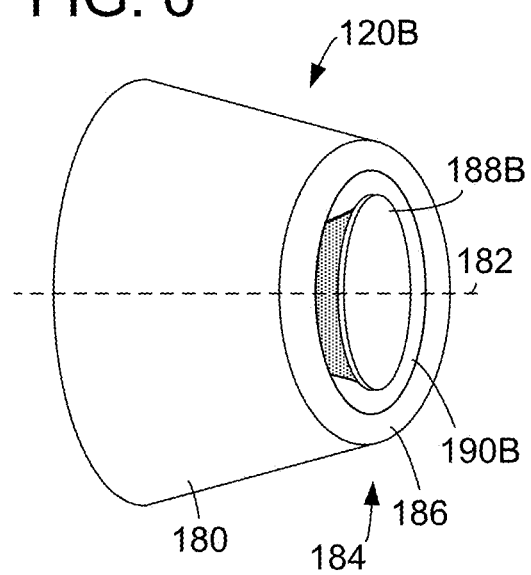
FIG. 6 is an illustration of a co-axial fiber spinneret shown in FIG. 1.

FIG. 6 is an illustration of a co-axial fiber spinneret 120B. Like solid fiber spinneret 120A, co-axial fiber spinneret 120B includes a truncated conical body 180 with an annulus 186 at a dispensing end 184. Co-axial fiber spinneret 120B also includes a central body 188B positioned within annulus 186. Annulus 186 and central body 188B define an annular aperture 190B. Accordingly, when polymer 140 is dispensed by co-axial fiber spinneret 120B, fibers 165 have a co-axial composition, with an exterior wall surrounding a cavity. The exterior wall of a fiber 165 dispensed by co-axial fiber spinneret 120B defines an outer diameter corresponding to the inner diameter of annulus 186 and an inner diameter corresponding to the diameter of central body 188B. Accordingly, the outer diameter and inner diameter of co-axial fibers 165 may be adjusted by adjusting the diameters of annulus 186 and central body 188B.

Fiber spinnerets 120A and 120B facilitate incorporating a substance, such as a biological agent, growth factor, and/or a drug (e.g., a chemotherapeutic substance), into patch 170. For example, the substance may be deposited within a cavity defined by co-axial fibers 165 of patch 170. In one embodiment, polymer 140 is selected to create porous and/or semi-soluble fibers 165, and the substance is dispensed from the cavity through fibers 165. In another embodiment, polymer 140 is degradable, and the substance is dispensed as fibers 165 degrade in vivo. For example, fibers 165 may be configured to degrade within a second to 1 second to 12 months. In one embodiment, a burst release of the substance occurs upon entry into a system and an elution occurs over a predetermined period of time. The degradation rate of polymer 140 may be manipulated by any loading and/or release method such as adjusting a ratio of constituent polymers within polymer 140, loading the agent into the bulk of the material, functionalizing the agent to the surface of the fibers, and/or releasing the agent by degradation of the polymer or by diffusion of the agent from the polymer. In another embodiment, a substance is delivered by solid fibers 165. For example, a solid fiber 165 may be created from a polymer 140 including the substance in solution. As solid fiber 165 degrades, the substance is released into the surrounding tissue.

As shown in FIGS. 5 and 6, annulus 186 is perpendicular to center line 182. In an alternative embodiment, annulus 186 is oblique (e.g., oriented at an acute or obtuse angle) with respect to center line 182. The outside diameter of fibers 165 may be determined by the inside diameter of annulus 186.

Figure 7:
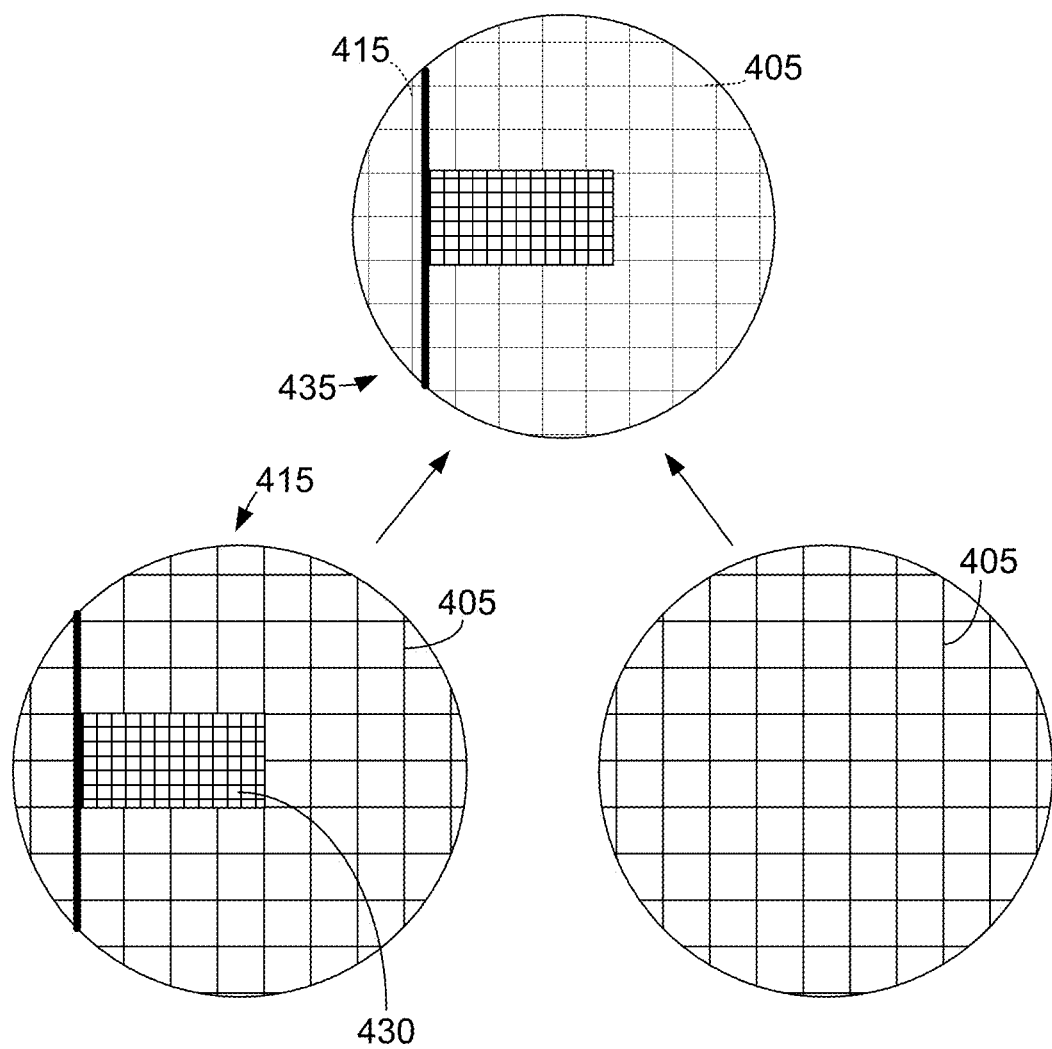
FIG. 7 is an illustration of a multi-layer biomedical patch.

FIG. 7 is an illustration of a multi-layer biomedical patch 435. Patch 435 includes a biomedical patch layer with a plurality of symmetrical spatially organized fibers 420 and a biomedical patch layer with a plurality of spatially organized fibers having varying densities 425 such as increased density portions 430. As shown in FIG. 7, biomedical patch layers 420 and 425 are combined (e.g., fused, joined, adhered, overlaid) to produce multi-layer biomedical patch 435 with reinforcement fiber layers. It should be noted that any combination, number, or type of fiber layers may be combined to create biomedical patch 435. Combining the patches, especially layers 420 and 425, facilitates providing a biomedical patch that promotes cell migration to a center of the biomedical patch while exhibiting potentially greater durability (e.g., tensile strength) than a biomedical patch having only standard, randomly-organized fibers. It should be noted that patch 435 can be formed of layers having various densities and/or thicknesses (both individually and collectively), fiber organizations, polymer compositions, surface coatings, and types of concentrations of agents and/or drugs.

In some embodiments, multiple biomedical patch layers 410-425 may be combined to create a multi-layer biomedical patch. For example, referring to FIGS. 1-4, after depositing a first set of fibers on collector 105, one may wait for the first set of fibers 165 to solidify completely or cure and then deposit a second set of fibers 165 on collector 105. The second set of fibers 165 may be deposited directly over the first set of fibers 165 on collector 105. Alternatively, the first set of fibers 165 may be removed from collector 105, and the second set of fibers 165 may be deposited on conductive surface 162 and/or collector 105 and then removed and adhered/overlaid on the first set of fibers 165. Such embodiments facilitate increased structural or mechanical reinforcement of the patch in predetermined locations, and added spatial control of cell migration/activity imparted by the layers 2-dimensionally and stacked layers 3-dimensionally. In some embodiments, a non nanofiber intermediate layer (e.g., hydrogel or polymeric scaffold) may be disposed between biomedical patch layers 400 and/or biomedical patch layers 410.

In the exemplary embodiment, individual layers are fused or coupled together such that the layers delaminate or separate under specific environmental or temporal conditions. Such controlled delamination results in maximization of mechanical stability of the nanofiber material and the biological interaction (e.g. cellular ingrowth, tissue integration, cellular exposure, etc.) between adjacent layers of nanofibers. In the exemplary embodiment, the process of fusing or coupling layers includes, but is not limited to, heating, applying mechanical stress/pressure, applying an adhesive, chemical processing, cross-linking, and functionalization.

Figure 8:
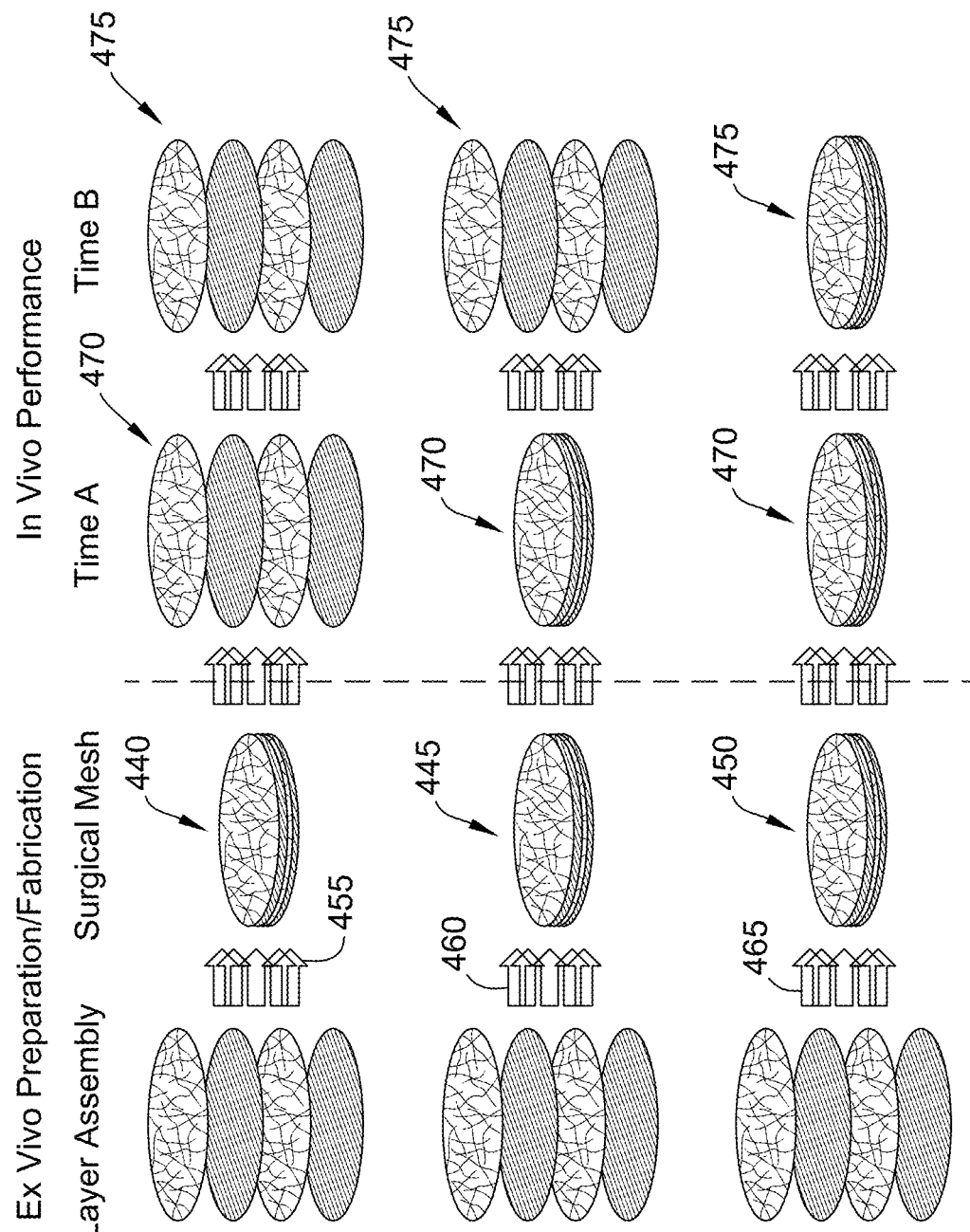
FIG. 8 is an illustration of a delamination of patches, such as the patch shown in FIG. 7, using various fusion strengths over time.

In one embodiment, adjacent layers are similarly or variably fused, adhered, or joined such that each layer delaminates or separates at a substantially similar rate within patch 435. Alternatively, layers can be fused together with variable methods such that each layer delaminates at different rates. FIG. 8 illustrates delamination of patches 440, 445, and 450 with various fusion strengths over time. In the exemplary embodiment, a low strength adhesion 455, such as but not limited to mild-chemical treatment or crosslinking, low-pressure physical lamination, or low-temperature thermal processing, is used to fuse layers of patch 440 together. Similarly, a moderate strength adhesion 460 such as but not limited to moderate chemical crosslinking, prolonged thermal processing, moderate mechanical entanglement, application of moderate adhesives, or high-pressure physical lamination is used to fuse the layers of patch 445 and a high strength adhesion 465, such as but not limited to extensive chemical crosslinking, extensive high-temperature thermal processing, extensive mechanical entanglement, fiber interweaving or knitting, or application of aggressive adhesives is used to fuse layers of patch 450 together. In the exemplary embodiment, a separation 470 of patches 440, 445, and 450 is shown after a short increment of time, such as, but not limited to 1 day-30 days and a separation 475 of patches 440, 445, and 450 is shown after a long increment of time, such as, but not limited to 30 days-3 years. As is shown, patch 440 is substantially separated 470 after a short period of time acting as an accelerated separation, patch 445 is substantially separated 475 after the long period of time acting as a delayed separation, and patch 450 provided substantially no separation.

Figure 9:
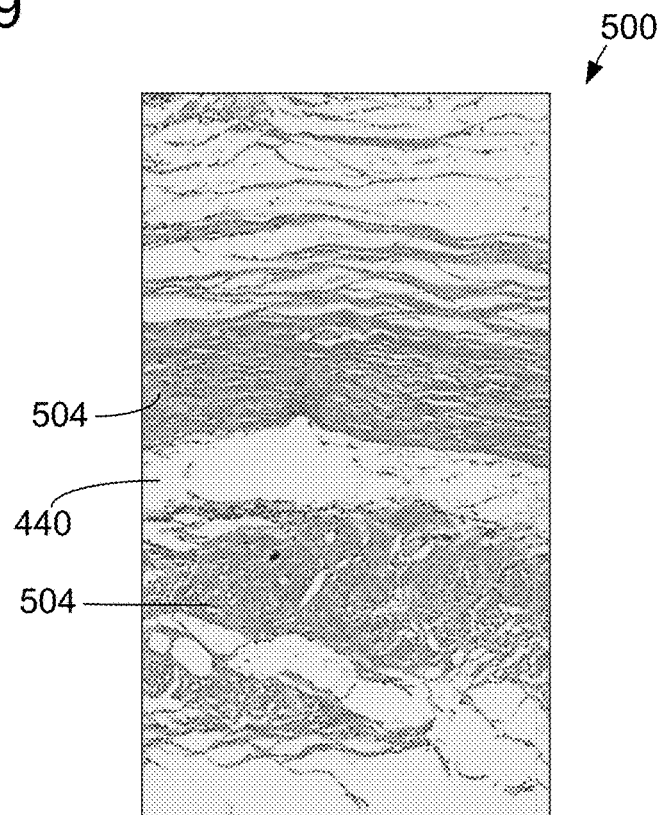
FIGS. 9 and 10 are histological cross-sections of regenerated dura repaired with multi-laminar nanofiber material such as a patch shown in FIG. 8.
Figure 10:
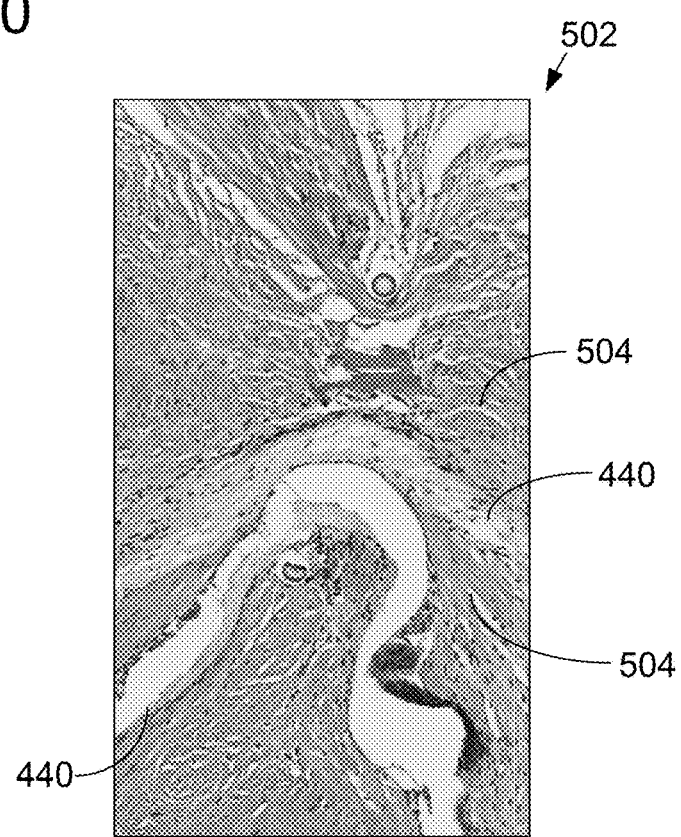

FIGS. 9 and 10 are histological cross-sections 500 and 502 of dura mater repaired with multi-laminar nanofiber material such as patch 440 shown in FIG. 8. Referring to FIG. 9, patch 440 is shown as being inserted into dura 504 two weeks post-operatively. Regenerative dural tissue ("neodura") 504 is demonstrated extending on and around the implanted nanofiber material 440. Regenerative dural fibroblasts are also shown to have penetrated the bulk of the nanofiber material 440, demonstrating progressive cellularization of the implanted nanofiber construct. Two weeks following implantation of the multi-layer nanofiber material 440 no delamination is noted upon histological examination of the explanted tissue. The nanofiber material 440 is observed as a homogeneous block of material with low to moderate cellular ingrowth, yet no singular nanofiber layer or separation of nanofiber layers is observed. FIG. 10 illustrates controlled delamination of patch 440 six weeks post-operatively and integration of the patch within the native and/or regenerated dural tissue 504. Regenerative dural tissue ("neodura") 504 is demonstrated extending on and around the implanted nanofiber material 440. Additionally, regenerative dural tissue ("neodura") is demonstrated extending in between delaminated layers of the nanofiber material. Regenerative dural fibroblasts are shown to have significantly penetrated the bulk of the nanofiber material 440, demonstrating robust cellularization and integration of the implanted nanofiber construct. Delamination of individual layers of nanofibers within the implant construct is noted upon histological examination of the explanted tissue. The nanofiber material 440 is observed as two heterogeneous layers of material separated by a thin layer of regenerated dural tissue extending along the adjoining surface of the nanofiber monolayers. Evidence of controlled delamination of the implanted material post-operatively is specifically demonstrated by observation that multiple layers of the material remain fused in proximity of sutures utilized to secure the material to the native tissue.

Figure 11:
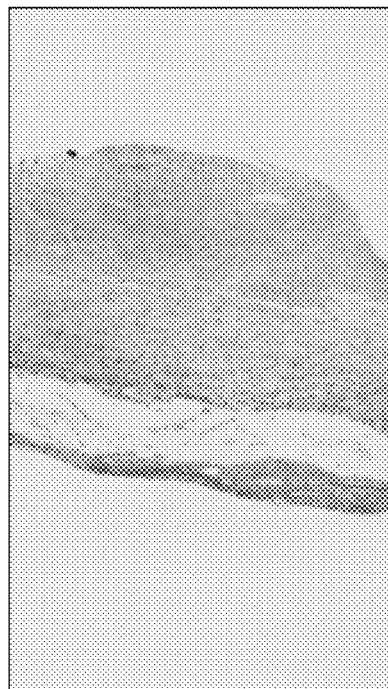
FIGS. 11 and 12 are histological cross-sections of regenerated dura repaired with multi-laminar nanofiber material such as a patch shown in FIG. 8.
Figure 12:

FIGS. 11 and 12 are histological cross-sections 506 and 508 of regenerated dura repaired with multi-laminar nanofiber material such as patch 450 shown in FIG. 8. Referring to FIG. 11, patch 450 is shown as being inserted into dura 504 two weeks post-operatively. Regenerative dural tissue ("neodura") 504 is demonstrated extending on and around the implanted nanofiber material 450. Regenerative dural fibroblasts are also shown to have penetrated the bulk of the nanofiber material 450, demonstrating cellularization of the implanted nanofiber construct. No delamination is noted upon histological examination of the explanted tissue. The nanofiber material 450 is observed as a homogeneous block of material with low to moderate cellular ingrowth, yet no singular nanofiber layer or separation of nanofiber layers is observed. FIG. 12 illustrates that the high strength adhesion has enabled layers of patch 450 to remain substantially fused together six week post-operatively as dural tissue 504 regenerated around patch 450. Regenerative dural tissue ("neodura") 504 is again demonstrated extending on and around the implanted nanofiber material 450. Dural fibroblasts substantially penetrate the bulk of the nanofiber material 450, demonstrating robust cellularization of the implanted nanofiber construct. Unlike nanofiber patch 440, no delamination of nanofiber patch 450 is noted upon histological examination of the explanted tissue following chronic implantation. The nanofiber material 450 is observed as a secure composite material demonstrating cellular ingrowth yet no separation or observation of singular nanofiber layers.

Figure 13:
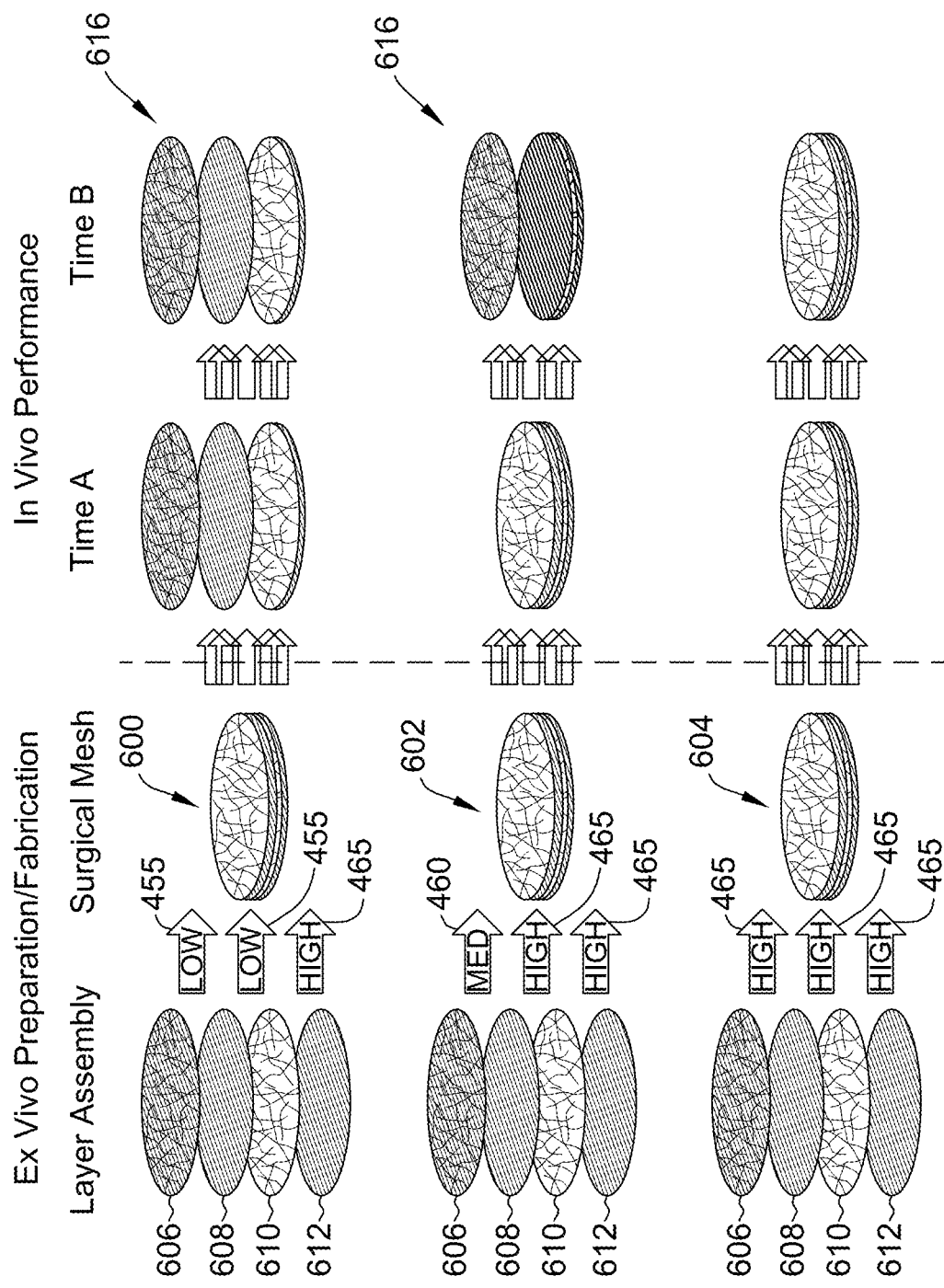
FIG. 13 is an illustration of a delamination of patches, such as the patch shown in FIG. 7, using various fusion methods and strengths over time.

FIG. 13 illustrates separation of layers within patches 600, 602, and 604 at varying rates. Each patch 600, 602, and 604 includes a first layer 606, a second layer, 608, a third layer 610, and a fourth layer 612. It should be noted that while patches 600, 602, and 604 are shown with four layers, patches can be fabricated to have any number of layers. Referring to patch 600, low strength adhesion 455 is used to fuse layers 606, 608, and 610 together and high strength adhesion 465 is used to fuse layers 610 and 612 together. After a short time period, a separation 614 of layers 606, 608, and 610 has occurred and layers remain substantially fused together. As shown in patch 602, moderate strength adhesion 460 is used to fuse together layers 606 and 608, while high strength adhesion 465 is used to fuse together layers 608, 610, and 612. A separation 616 of layers 606 and 608 occurs after a long period of time while substantially no separation occurs between layers 608, 610, and 612. Referring to patch 604, a high strength adhesion 465 is used between layers 606, 608, 610, and 612 such that substantially no separation occurs between the layers.

A multi-layered biomedical patch may be useful for dural grafts as well as other tissue engineering applications. Sequential layers of fibers can be created with varying orders (e.g., radially aligned, reinforced, or randomly oriented), densities (e.g., low, high, or mixture of fiber density), patterns or reinforcement, and compositions (polymer), which may allow specific types of cells to infiltrate and populate select layers of the artificial biomedical patch. For example, biomedical patches containing a high fiber density generally prohibit cellular migration and infiltration, while biomedical patches containing a low fiber density generally enhance cellular migration and infiltration. Such additional support and/or reinforcement properties are achieved by creating high density fiber deposition that discourages cellular penetration and having low density fiber deposition areas that promote cellular penetration and/or ingrowth.

Overall, the ability to form multi-layered fiber materials, as described herein, may be extremely beneficial in the construction of biomedical patches designed to recapitulate the natural multi-laminar structure of not only dura mater, but also other biological tissues such as skin, heart valve leaflets, pericardium, and/or any other biological tissue. Furthermore, one or more layers of a biomedical patch may be fabricated from bioresorbable polymers such that the resulting nanofiber materials fully resorb following implantation. Manipulation of the chemical composition of the polymers utilized to fabricate these scaffolds may further allow for specific control of the rate of degradation and/or resorption of a biomedical patch following implantation.

Figure 14:
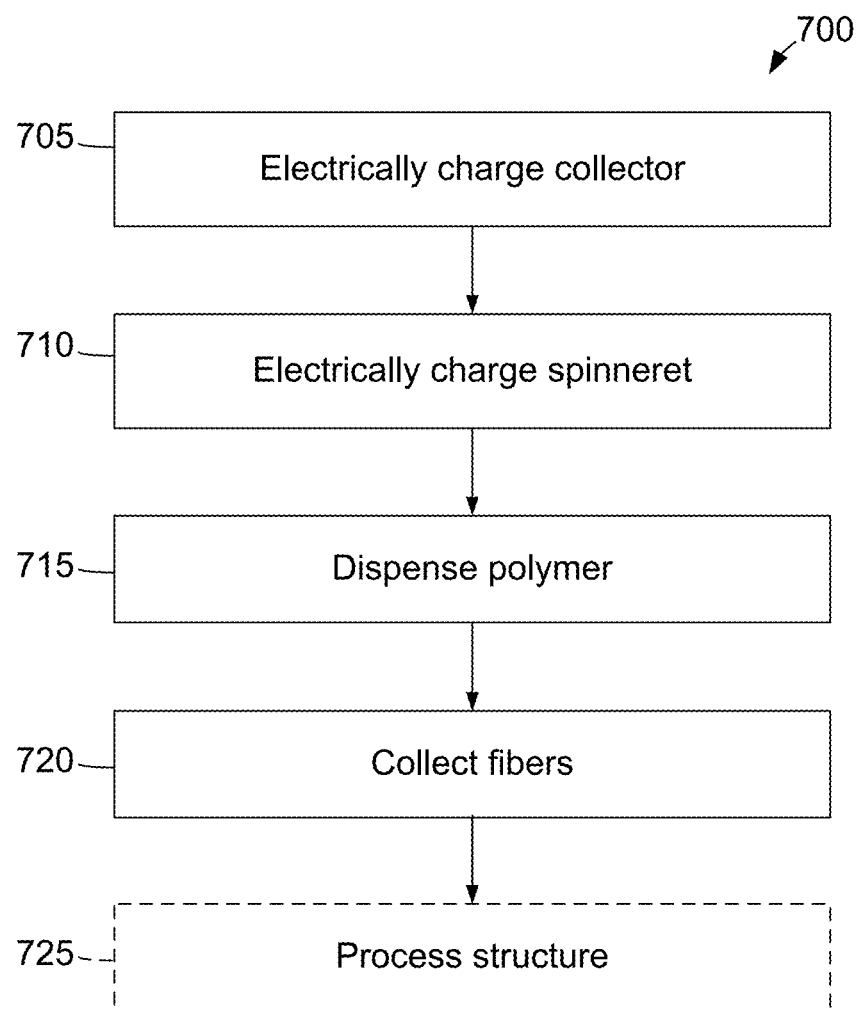
FIG. 14 is a flowchart of an exemplary method 700 for producing a structure of spatially arranged fibers using system 100 shown in FIG. 1.

FIG. 14 is a flowchart of an exemplary method 700 for producing a structure of spatially organized fibers using system 100 shown in FIG. 1. While one embodiment of method 700 is shown in FIG. 14, it is contemplated that any of the operations illustrated may be omitted and that the operations may be performed in a different order than is shown. In the exemplary embodiment, method 700 includes electrically charging 705 collector 105 at a first amplitude and/or polarity (e.g., negatively charging or grounding). Spinneret 120 is electrically charged 710 at a second amplitude and/or polarity opposite the first amplitude and/or polarity (e.g., positively charged). A polymer (e.g., a liquid polymer) is dispensed 715 from spinneret 120. In the exemplary embodiment, dispensed 715 polymers are collected 720 on collector 105 to form a plurality of polymeric fibers on or substantially near features 112 that creates a structure or patch. After the dispensed 615 polymers are collected 720 and a structure is created, the structure may undergo post-processing 725. Such post-processing 725 can include, but is not limited to, lamination, layer stacking, coupling and/or fusing, chemically treating, and applying a biological agent, growth factor, and/or drug.

Figure 15:
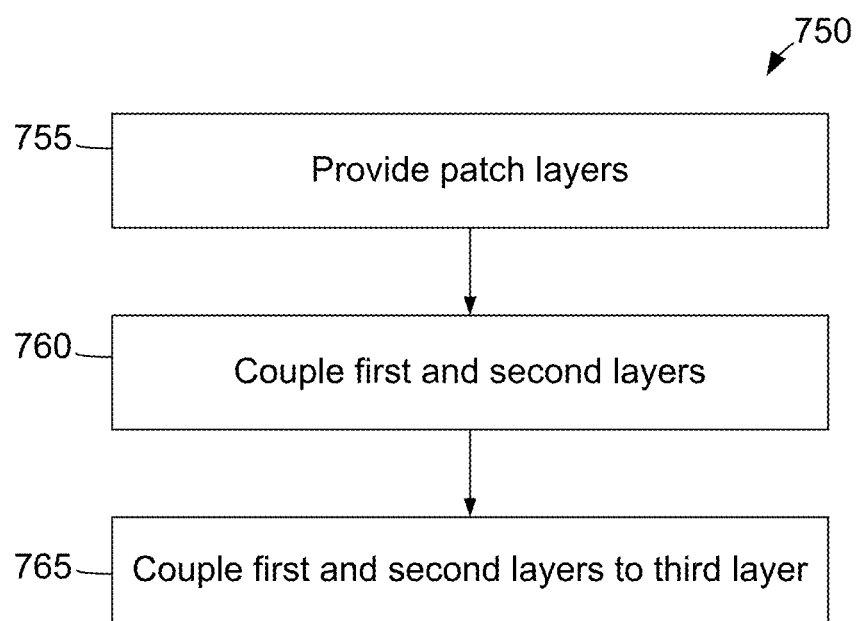
FIG. 15 is a flowchart of an exemplary method 750 for fusing or coupling together structures or patch layers produced by method 700 shown in FIG. 14.

FIG. 15 is a flowchart of an exemplary method 750 for fusing or coupling together structures or patch layers produced by method 700 shown in FIG. 14. Method 750 includes providing 755 a first, second, and third patch layer. First patch layer is coupled 760 to second patch layer using a first coupling technique. The coupled 760 first and second layers are then coupled 765 to the third patch layer using a second coupling technique different than the first coupling technique. In the exemplary embodiment, coupling techniques, include but are not limited to, heating, applying mechanical stress/pressure, chemical processing, cross-linking, and functionalization. While method 750 illustrates a first patch layer coupled to a second patch layer, it should be noted that multiple layers (e.g., 3, 5, 6) can be coupled together simultaneously. Additionally, the process may be repeated to add layers to structures produced by method 750.

Figure 16:
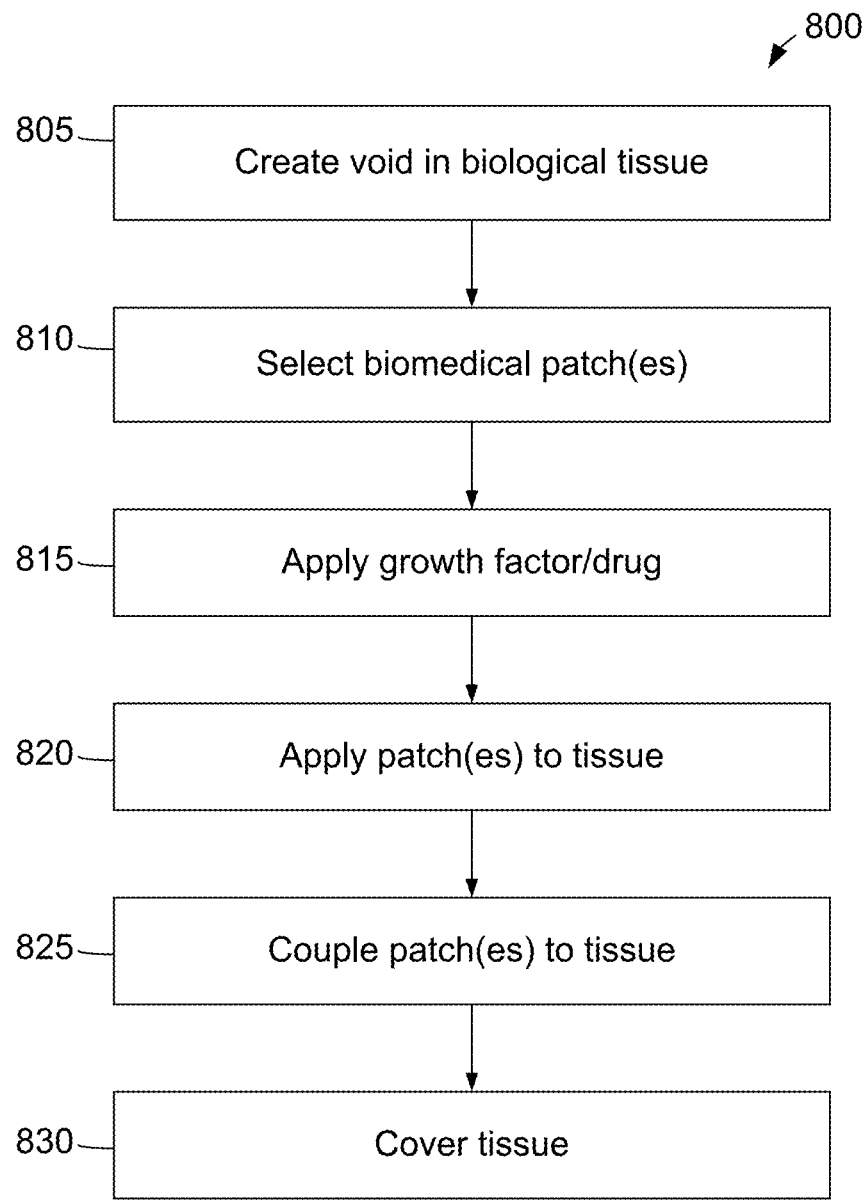
FIG. 16 is a flowchart of an exemplary method 800 for repairing a defect in a biological tissue using the structures produced by methods 700 and 750 shown in FIGS. 14 and 15.

FIG. 16 is a flowchart of an exemplary method 800 for repairing a defect of a substrate using a structure produced by methods 700 and 750 shown in FIGS. 14 and 15. In one embodiment, method 800 includes providing 805 a substrate substance with a defect. The defect may include a void, tissue defect, injury, insult, and/or any other condition resulting in diminished function of biological tissue. In the exemplary embodiment, the substrate is biological tissue. Alternatively, the substrate can be any substrate including but not limited to, filtration media, textiles, membrane media, and coatings. In one embodiment, the defect provided 805 includes a void created by surgical incision to provide access to an underlying tissue (e.g., a tumor). In another embodiment, a void is created 805 by excising necrotic tissue (e.g., skin cells). In the exemplary embodiment, one or more patches capable of covering the defect are selected 810. For example, a plurality of biomedical patches may be selected 810 for a large and/or complex (e.g., irregularly shaped) defect. In the exemplary embodiment, a biomedical patch having a diameter greater than the diameter of an approximately circular defect is selected 810. Alternatively, a patch is selected 810 and customized, pre-operation or intra-operation, to fit the defect. It should be noted that any size, shape, and/or geometry of structure may be used in the selection 810 of the patch.

In one embodiment, a substance such as a growth factor and/or a drug (e.g., a chemotherapeutic drug) is applied 815 to the biomedical patch. In the exemplary embodiment growth factor and/or a drug is applied 815 pre-operatively. However, it should be noted that growth factor and/or a drug may be applied 815 at any time including, but not limited to, intra-operatively and post-operatively. In one embodiment, the biomedical patch may be immersed in the substance to allow the substance to occupy a cavity within co-axial fibers of the biomedical patch, dope the polymer comprising the fibers in the biomedical patch, or coat the surface of the fibers within the biomedical patch.

In the exemplary embodiment, the patch is applied 820 to (e.g., overlaid on) the biological tissue to cover, repair, reinforce, and/or fill at least a portion of the defect. For example, the biomedical patch may be applied 820 to dura mater tissue, cardiac tissue, and/or any biological tissue including a defect. In one embodiment, the perimeter of the biomedical patch extends past the perimeter of the defect, such that the entire defect is covered by the biomedical patch. In some embodiments, the biomedical patch is coupled 825 to the biological tissue with a plurality of sutures, adhesive, and/or any other means of attaching the biomedical patch to the biological tissue (inlay). In an alternative embodiment, the biomedical patch is simply allowed to fuse to the biological tissue, such as by adhesion of biological cells to the biomedical patch (onlay). In another embodiment, biomedical patch may be directly coupled to the edge of the tissue with no overlap. In one embodiment, biomedical patch may be overlaid on top of a wound/defect or injury covering the entirety of the defect or injury without filling the defect.

In one embodiment, after the biomedical patch is applied 820 and optionally coupled 825 to the biological tissue, the biological tissue is covered 830. Alternatively, the patch may be the terminal covering. In such an embodiment, a backing that is either non-permeable or permeable may be coupled to the patch. In one embodiment, other tissue overlaying the defect (e.g., dermis and/or epidermis) is repaired (e.g., sutured closed). In another embodiment, one or more protective layers are applied over the biological tissue. For example, a bandage may be applied to a skin graft, with or without a protective substance, such as a gel, an ointment, and/or an antibacterial agent. In one embodiment, the protective layer includes, but is not limited to, a covering, film tissue, dressing, mesh, and nanofiber structure, such as an additional biomedical patch, as described herein.

Embodiments described herein are operable with any surgical procedure involving the repair, replacement, or expansion of the dura mater, including, but not limited to, a transphenoidal procedure (e.g., surgical removal of pituitary adenomas), various types of skull base surgeries, and/or surgical removal of cranial or spinal tumors (e.g., meningiomas and/or astrocytomas). In one embodiment, a biomedical patch may be applied to a bone fracture (e.g., a complex fracture). In another embodiment, a biomedical patch may be applied to a defect in the skin (e.g. a burn).

Moreover, such embodiments provide a dura mater substitute, a biomedical patch for a skin graft (e.g., dermal or epidermal), a biomedical patch for tracheal repair, a scaffold for an artificial heart valve leaflet, an artificial mesh for surgical repair of a gastrointestinal tract (e.g., an abdominal hernia or an ulcer), an artificial mesh for surgical repair of cardiac defects. Embodiments described herein facilitate providing a cardiac patch of sufficient flexibility to enable movement of the biomedical patch by a biological tissue (e.g., cardiomyocytes or cardiac tissue, muscle, skin, connective tissue, intestinal tissue, stomach tissue, bone, gastrointestinal tract, and mucosa).

In some embodiments, a biomedical patch has a thickness greater or less than a thickness of the biological tissue being repaired. Biomedical patches with spatially organized polymeric fibers facilitate reducing the expense of tissue repair, improving tissue healing time, and reducing or eliminating the risk of zoonotic infection. Moreover, such biomedical patches are relatively simple to manufacture, enabling customization of shape, size, and chemical composition and improved availability and non-immunogenicity. In addition, biomedical patches with spatially organized polymeric fibers exhibit excellent handling properties due to their cloth-like composition, eliminate the need for a second surgery to harvest autologous graft tissue, and reduce the risk of contracture and adhesion when compared with known products. Additionally, the patches described herein facilitate reinforcement, buttressing, lamination, and/or sealing in a variety of applications such as but not limited to clinical and non-clinical applications.

Although the foregoing description contains many specifics, these should not be construed as limiting the scope of the present disclosure, but merely as providing illustrations of some of the presently preferred embodiments. Similarly, other embodiments of the invention may be devised which do not depart from the spirit or scope of the present invention. For example, while the illustrative examples have been used in with clinical applications, the above described nanofiber structures can have non-clinical application such as filtration, textiles, membrane technology, and coatings. Features from different embodiments may be employed in combination. The scope of the invention is, therefore, indicated and limited only by the appended claims and their legal equivalents, rather than by the foregoing description. All additions, deletions, and modifications to the invention as disclosed herein which fall within the meaning and scope of the claims are to be embraced thereby.

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A three-dimensional electrospun biomedical patch for facilitating tissue repair, the three-dimensional electrospun biomedical patch comprising:
a first polymeric plurality of fibers making up a scaffold, the scaffold comprising a first structure of deposited electrospun fibers, the first structure of deposited electrospun fibers comprising a plurality of deposited electrospun fibers extending in a plurality of directions in three dimensions to facilitate cellular migration for a first period of time upon application of the three-dimensional electrospun biomedical patch to a tissue, wherein the first period of time is less than twelve months;
a second polymeric plurality of fibers making up the scaffold, the scaffold further comprising a second structure of deposited electrospun fibers, the second polymeric plurality of fibers overlaid on the first polymeric plurality of fibers, the second polymeric plurality of fibers comprising one or more portions with a higher deposition of fibers than one or more portions of the first polymeric plurality of fibers, the second structure of deposited electrospun fibers comprising the plurality of deposited electrospun fibers configured to provide structural reinforcement for a second period of time upon application of the three-dimensional electrospun biomedical patch to the tissue, wherein the second period of time is less than twelve months;

the plurality of deposited electrospun fibers connecting the first polymeric plurality of fibers and the second polymeric plurality of fibers, the plurality of deposited electrospun fibers comprising a first set of deposited electrospun fibers generated by electrospinning a first polymer composition and a second set of deposited electrospun fibers generated by electrospinning a second polymer composition, wherein the first set of deposited electrospun fibers and the second set of deposited electrospun fibers are entangled, wherein the first set of deposited electrospun fibers and the second set of deposited electrospun fibers are bioresorbable; and a plurality of voids, the plurality of voids comprising one or more voids between 10 µm and 10 cm in length, wherein the three-dimensional electrospun biomedical patch is pliable and resistant to tearing to enable movement of the three-dimensional electrospun biomedical patch with the tissue.

2. The three-dimensional electrospun biomedical patch of claim 1, further comprising a spatial arrangement formed by one or more of the plurality of deposited electrospun fibers.

3. The three-dimensional electrospun biomedical patch of claim 2, wherein the spatial arrangement comprises an asymmetrical arrangement.

4. The three-dimensional electrospun biomedical patch of claim 2, wherein the spatial arrangement comprises a repeating pattern.

5. The three-dimensional electrospun biomedical patch of claim 2, wherein the spatial arrangement is formed by overlaying the second polymeric plurality of fibers on the first polymeric plurality of fibers.

6. The three-dimensional electrospun biomedical patch of claim 1, wherein the tissue comprises skin.

7. The three-dimensional electrospun biomedical patch of claim 1, wherein the tissue comprises one or more of skin, dura mater, heart valve leaflets, cardiac tissue, trachea, gastrointestinal tract, pericardium, muscle, connective tissue, intestinal tissue, stomach tissue, bone, gastrointestinal tract, or mucosa.

8. The three-dimensional electrospun biomedical patch of claim 1, wherein the first polymer composition comprises poly(lactic-co-glycolic acid).

9. The three-dimensional electrospun biomedical patch of claim 1, wherein the first polymer composition comprises glycolic acid, and wherein the second polymer composition comprises caprolactone.

10. The three-dimensional electrospun biomedical patch of claim 1, wherein the second polymeric plurality of fibers is overlaid on the first polymeric plurality of fibers by depositing the second structure of deposited electrospun fibers on the first structure of deposited electrospun fibers.

11. The three-dimensional electrospun biomedical patch of claim 1, further comprising one or more pores, wherein the one or more pores vary between 10 µm and 10 cm.

12. A three-dimensional electrospun biomedical patch for facilitating tissue repair, the three-dimensional electrospun biomedical patch comprising:

a first polymeric plurality of fibers making up a scaffold, the scaffold comprising a first structure of deposited electrospun fibers, the first structure of deposited electrospun fibers comprising a plurality of deposited electrospun fibers extending in a plurality of directions in three dimensions to facilitate cellular migration for a first period of time upon application of the three-dimensional electrospun biomedical patch to a tissue, wherein the first period of time is less than twelve months;

a second polymeric plurality of fibers making up the scaffold, the scaffold further comprising a second structure of deposited electrospun fibers, the second polymeric plurality of fibers overlaid on the first polymeric plurality of fibers, the second polymeric plurality of fibers comprising one or more portions with a higher deposition of fibers than one or more portions of the first polymeric plurality of fibers, the second structure of deposited electrospun fibers comprising the plurality of deposited electrospun fibers configured to provide structural reinforcement for a second period of time upon application of the three-dimensional electrospun biomedical patch to the tissue, wherein the second period of time is less than twelve months;

the plurality of deposited electrospun fibers connecting the first polymeric plurality of fibers and the second polymeric plurality of fibers, the plurality of deposited electrospun fibers comprising a first set of deposited electrospun fibers generated by electrospinning a first polymer composition and a second set of deposited electrospun fibers generated by electrospinning a second polymer composition, wherein the first set of deposited electrospun fibers and the second set of deposited electrospun fibers are entangled, wherein the first set of deposited electrospun fibers and the second set of deposited electrospun fibers are bioresorbable; and a plurality of pores, the plurality of pores comprising one or more pores between 10 µm and 10 cm in length, wherein the three-dimensional electrospun biomedical patch is pliable and resistant to tearing to enable movement of the three-dimensional electrospun biomedical patch with the tissue.

13. The three-dimensional electrospun biomedical patch of claim 12, further comprising a spatial arrangement formed by one or more of the plurality of deposited electrospun fibers.

14. The three-dimensional electrospun biomedical patch of claim 13, wherein the spatial arrangement comprises an asymmetrical arrangement.

15. The three-dimensional electrospun biomedical patch of claim 13, wherein the spatial arrangement comprises a repeating pattern.

16. The three-dimensional electrospun biomedical patch of claim 13, wherein the spatial arrangement comprises a symmetric arrangement.

17. The three-dimensional electrospun biomedical patch of claim 13, wherein the spatial arrangement is formed by overlaying the second polymeric plurality of fibers on the first polymeric plurality of fibers.

18. The three-dimensional electrospun biomedical patch of claim 12, wherein the tissue comprises skin.

19. The three-dimensional electrospun biomedical patch of claim 12, wherein the tissue comprises one or more of skin, dura mater, heart valve leaflets, cardiac tissue, trachea, gastrointestinal tract, pericardium, muscle, connective tissue, intestinal tissue, stomach tissue, bone, gastrointestinal tract, or mucosa.

20. The three-dimensional electrospun biomedical patch of claim 12, wherein the first polymer composition comprises poly(lactic-co-glycolic acid).

21. The three-dimensional electrospun biomedical patch of claim 12, wherein the first polymer composition comprises glycolic acid, and wherein the second polymer composition comprises caprolactone.

22. A three-dimensional electrospun biomedical patch for facilitating tissue repair, the three-dimensional electrospun biomedical patch comprising:
   a first polymeric plurality of fibers making up a scaffold, the scaffold comprising a first structure of deposited electrospun fibers, the first structure of deposited electrospun fibers comprising a plurality of deposited electrospun fibers extending in a plurality of directions in three dimensions to facilitate cellular migration for a first period of time upon application of the three-dimensional electrospun biomedical patch to a tissue, wherein the first period of time is less than twelve months;
   a second polymeric plurality of fibers making up the scaffold, the scaffold further comprising a second structure of deposited electrospun fibers, the second polymeric plurality of fibers overlaid on the first polymeric plurality of fibers, the second polymeric plurality of fibers comprising one or more portions with a higher deposition of fibers than one or more portions of the first polymeric plurality of fibers, the second structure of deposited electrospun fibers comprising the plurality of deposited electrospun fibers configured to provide structural reinforcement for a second period of time upon application of the three-dimensional electrospun biomedical patch to the tissue, wherein the second period of time is less than twelve months; and
   the plurality of deposited electrospun fibers connecting the first polymeric plurality of fibers and the second polymeric plurality of fibers, the plurality of deposited electrospun fibers comprising a first set of deposited electrospun fibers generated by electrospinning a first polymer composition and a second set of deposited electrospun fibers generated by electrospinning a second polymer composition, wherein the first set of deposited electrospun fibers and the second set of deposited electrospun fibers are entangled, wherein the first set of deposited electrospun fibers and the second set of deposited electrospun fibers are bioresorbable wherein the plurality of deposited electrospun fibers are deposited in an arrangement comprising a plurality of void slits between 10 μm and 10 cm in length;
   wherein the three-dimensional electrospun biomedical patch is pliable and resistant to tearing to enable movement of the three-dimensional electrospun biomedical patch with the tissue.

23. The three-dimensional electrospun biomedical patch of claim 22, further comprising a spatial arrangement formed by one or more of the plurality of deposited electrospun fibers.

24. The three-dimensional electrospun biomedical patch of claim 23, wherein the spatial arrangement comprises an asymmetrical arrangement.

25. The three-dimensional electrospun biomedical patch of claim 23, wherein the spatial arrangement comprises a repeating pattern.

26. The three-dimensional electrospun biomedical patch of claim 23, wherein the spatial arrangement comprises a symmetric pattern.

27. The three-dimensional electrospun biomedical patch of claim 23, wherein the spatial arrangement is formed by overlaying the second polymeric plurality of fibers on the first polymeric plurality of fibers.

28. The three-dimensional electrospun biomedical patch of claim 22, wherein the tissue comprises skin.

29. The three-dimensional electrospun biomedical patch of claim 22, wherein the tissue comprises one or more of skin, dura mater, heart valve leaflets, cardiac tissue, trachea, gastrointestinal tract, pericardium, muscle, connective tissue, intestinal tissue, stomach tissue, bone, gastrointestinal tract, or mucosa.

30. The three-dimensional electrospun biomedical patch of claim 22, wherein the first polymer composition comprises poly(lactic-co-glycolic acid).

31. The three-dimensional electrospun biomedical patch of claim 22, wherein the first polymer composition comprises glycolic acid, and wherein the second polymer composition comprises caprolactone.

* * * * *